United States Patent
Ferrer et al.

(10) Patent No.: US 10,064,767 B2
(45) Date of Patent: Sep. 4, 2018

(54) DIAPER STRUCTURE WITH ENHANCED TACTILE SOFTNESS ATTRIBUTES AND PROVIDING RELATIVELY LOW HUMIDITY

(71) Applicant: The Procter & Gamble Company, Cincinnati, OH (US)

(72) Inventors: John Ferrer, Mason, OH (US); Sharon Ann Young, Mason, OH (US); Mike P Purdon, Hebron, KY (US); Han Xu, Cincinnati, OH (US); Paul Thomas Weisman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 155 days.

(21) Appl. No.: 14/614,836

(22) Filed: Feb. 5, 2015

(65) Prior Publication Data
US 2015/0182387 A1 Jul. 2, 2015

Related U.S. Application Data

(63) Continuation-in-part of application No. 13/953,772, filed on Jul. 30, 2013.
(Continued)

(51) Int. Cl.
*A61F 13/514* (2006.01)
*A61F 13/511* (2006.01)
(Continued)

(52) U.S. Cl.
CPC ...... *A61F 13/51401* (2013.01); *A61F 13/513* (2013.01); *A61F 13/51121* (2013.01);
(Continued)

(58) Field of Classification Search
CPC .......... A61F 13/51121; A61F 13/51456; A61F 13/51476; A61F 13/55105;
(Continued)

(56) References Cited

U.S. PATENT DOCUMENTS 3,333,315 A   8/1967   Dyer et al.
3,860,003 A   1/1975   Buell
(Continued)

FOREIGN PATENT DOCUMENTS

CA   2294922   12/1998
EP   1920232   4/2010
(Continued)

OTHER PUBLICATIONS

PCT International Search Report and Written Opinion, dated Oct. 7, 2013 (10 pages).
(Continued)

*Primary Examiner* — Peter S Vasat
(74) *Attorney, Agent, or Firm* — Christian M. Best

(57) ABSTRACT

A disposable diaper is provided. The diaper comprises a topsheet comprising a first nonwoven web. The topsheet has a basis weight greater than 25 gsm, according to the Basis Weight Test herein. The diaper comprises a backsheet comprising a second nonwoven web and a film. The film has a WVTR value of less than 6,500 $g/m^2$, according to the WVTR Test herein. The diaper comprises an absorbent core comprising an absorbent particulate polymer material disposed between the topsheet and the backsheet. The absorbent core is substantially cellulose free. The diaper has a relative humidity of less than 75%, according to the Humidity Test herein.

46 Claims, 15 Drawing Sheets

Related U.S. Application Data

(60) Provisional application No. 61/678,163, filed on Aug. 1, 2012.

(51) Int. Cl.

| | | |
|---|---|---|
| *A61F 13/551* | (2006.01) | |
| *A61F 13/513* | (2006.01) | |
| *A61L 15/24* | (2006.01) | |
| *A61L 15/22* | (2006.01) | |
| *A61F 13/51* | (2006.01) | |
| *A61F 13/539* | (2006.01) | |
| *A61F 13/531* | (2006.01) | |
| *A61F 13/53* | (2006.01) | |
| *A61F 13/15* | (2006.01) | |
| *A61F 13/84* | (2006.01) | |

(52) U.S. Cl.
CPC .. *A61F 13/51456* (2013.01); *A61F 13/51476* (2013.01); *A61F 13/51478* (2013.01); *A61F 13/55105* (2013.01); *A61L 15/225* (2013.01); *A61L 15/24* (2013.01); *A61F 13/531* (2013.01); *A61F 2013/15406* (2013.01); *A61F 2013/51019* (2013.01); *A61F 2013/51045* (2013.01); *A61F 2013/51078* (2013.01); *A61F 2013/51338* (2013.01); *A61F 2013/51452* (2013.01); *A61F 2013/530481* (2013.01); *A61F 2013/53908* (2013.01); *A61F 2013/8491* (2013.01)

(58) Field of Classification Search
CPC .. A61F 2013/15406; A61F 2013/51019; A61F 2013/51045; A61F 2013/51338; A61F 2013/51452; A61F 2013/530481; A61F 2013/8491
See application file for complete search history.

(56) References Cited

U.S. PATENT DOCUMENTS

| | | | |
|---|---|---|---|
| 4,430,148 A | 2/1984 | Schaefer et al. | |
| 4,519,799 A | 5/1985 | Sakurai et al. | |
| 4,940,464 A | 7/1990 | Van Gompel et al. | |
| 5,037,416 A | 8/1991 | Allen et al. | |
| 5,092,861 A | 3/1992 | Nomura et al. | |
| 5,151,092 A | 9/1992 | Buell et al. | |
| 5,246,433 A | 9/1993 | Hasse et al. | |
| 5,266,392 A | 11/1993 | Land et al. | |
| 5,269,775 A | 12/1993 | Freeland et al. | |
| 5,370,764 A | 12/1994 | Alikhan | |
| 2,705,687 A | 4/1995 | Petterson et al. | |
| 5,516,572 A * | 5/1996 | Roe | A61F 13/513 |
| | | | 428/131 |
| 5,554,145 A | 9/1996 | Roe et al. | |
| 5,569,234 A | 10/1996 | Buell et al. | |
| 5,571,096 A | 11/1996 | Dobrin et al. | |
| 5,607,760 A | 3/1997 | Roe | |
| 5,620,779 A | 4/1997 | Levy et al. | |
| 5,635,191 A | 6/1997 | Roe et al. | |
| 5,643,588 A | 7/1997 | Roe et al. | |
| 5,897,545 A | 4/1999 | Kline et al. | |
| 5,957,908 A | 9/1999 | Kline et al. | |
| 6,004,306 A | 12/1999 | Robles et al. | |
| 6,120,487 A | 9/2000 | Ashton | |
| 6,120,489 A | 9/2000 | Johnson et al. | |
| 6,156,024 A | 12/2000 | Schulte et al. | |
| 6,403,857 B1 * | 6/2002 | Gross | A61F 13/534 |
| | | | 604/365 |
| 6,446,495 B1 | 9/2002 | Herrlein et al. | |
| 6,479,415 B1 * | 11/2002 | Erspamer | A61F 13/534 |
| | | | 442/381 |
| 6,528,439 B1 | 3/2003 | Stokes et al. | |
| 6,573,423 B1 | 6/2003 | Herrlein et al. | |
| 6,610,390 B1 | 8/2003 | Kauschke et al. | |
| 6,632,385 B2 | 10/2003 | Kauschke et al. | |
| 6,645,569 B2 | 11/2003 | Cramer et al. | |
| 6,652,501 B2 | 11/2003 | Malchow et al. | |
| 6,686,512 B2 * | 2/2004 | Herrlein | A61F 13/15203 |
| | | | 604/368 |
| 6,803,103 B2 | 10/2004 | Kauschke et al. | |
| 6,837,961 B2 | 1/2005 | Malchow et al. | |
| 6,861,571 B1 | 3/2005 | Roe et al. | |
| 6,863,933 B2 | 3/2005 | Cramer et al. | |
| 6,872,274 B2 | 3/2005 | Kauschke et al. | |
| 7,112,621 B2 | 9/2006 | Rohrbaugh et al. | |
| 7,258,758 B2 | 8/2007 | Collier et al. | |
| 7,553,532 B2 | 6/2009 | Turner et al. | |
| 7,712,640 B2 | 5/2010 | Honer et al. | |
| 7,744,576 B2 | 6/2010 | Busam et al. | |
| 7,750,203 B2 | 7/2010 | Becker et al. | |
| 7,789,870 B2 | 9/2010 | Horn et al. | |
| 7,803,244 B2 | 9/2010 | Siqueira et al. | |
| 7,851,668 B2 | 12/2010 | Elder et al. | |
| 7,858,544 B2 | 12/2010 | Turi et al. | |
| 8,093,163 B2 | 1/2012 | Turi et al. | |
| 8,722,963 B2 | 5/2014 | Kanya et al. | |
| 2003/0097107 A1 | 5/2003 | Sprengard-Eichel et al. | |
| 2003/0148684 A1 | 8/2003 | Cramer et al. | |
| 2003/0157859 A1 * | 8/2003 | Ishikawa | A61F 13/51 |
| | | | 442/340 |
| 2003/0181112 A1 | 9/2003 | Ishikawa et al. | |
| 2003/0233082 A1 | 12/2003 | Kline et al. | |
| 2004/0175343 A1 | 9/2004 | Osborne et al. | |
| 2004/0242105 A1 * | 12/2004 | McGuire | D04H 1/54 |
| | | | 442/327 |
| 2005/0159720 A1 | 7/2005 | Gentilcore et al. | |
| 2006/0247599 A1 * | 11/2006 | Mullen | A61F 13/505 |
| | | | 604/393 |
| 2006/0253092 A1 | 11/2006 | Ponomarenko et al. | |
| 2007/0021022 A1 | 1/2007 | Kishine et al. | |
| 2007/0048709 A1 | 3/2007 | Ales et al. | |
| 2007/0233027 A1 | 10/2007 | Roe et al. | |
| 2007/0275622 A1 | 11/2007 | Masuda et al. | |
| 2008/0095978 A1 | 4/2008 | Siqueira et al. | |
| 2008/0306463 A1 | 12/2008 | Dent et al. | |
| 2008/0312623 A1 | 12/2008 | Hundorf et al. | |
| 2008/0318024 A1 | 12/2008 | Angadjivand et al. | |
| 2009/0118689 A1 | 5/2009 | Lawson et al. | |
| 2010/0249740 A1 * | 9/2010 | Miyamoto | A61F 13/51104 |
| | | | 604/384 |
| 2010/0305543 A1 | 12/2010 | Klaska | |
| 2011/0073513 A1 * | 3/2011 | Weisman | A61F 13/53 |
| | | | 206/494 |
| 2011/0282313 A1 | 11/2011 | Lu et al. | |
| 2012/0177886 A1 * | 7/2012 | Kanya | A61F 13/51476 |
| | | | 428/156 |
| 2013/0102986 A1 | 4/2013 | Ruiz et al. | |
| 2013/0253461 A1 | 9/2013 | Xu et al. | |
| 2014/0039434 A1 | 2/2014 | Xu et al. | |
| 2015/0148763 A1 | 5/2015 | Xu et al. | |

FOREIGN PATENT DOCUMENTS

| | | |
|---|---|---|
| WO | WO 1995-016746 | 6/1995 |
| WO | WO-1998058606 | 12/1998 |
| WO | WO 2000-069481 A1 | 11/2000 |
| WO | WO-2007027219 | 3/2007 |
| WO | WO 2007-097467 A1 | 8/2007 |
| WO | WO-2014/022652 | 2/2014 |

OTHER PUBLICATIONS

All Office Actions, Responses and Claims, U.S. Appl. No. 13/953,772.

All Office Actions, Responses and Claims, U.S. Appl. No. 14/608,321.

* cited by examiner

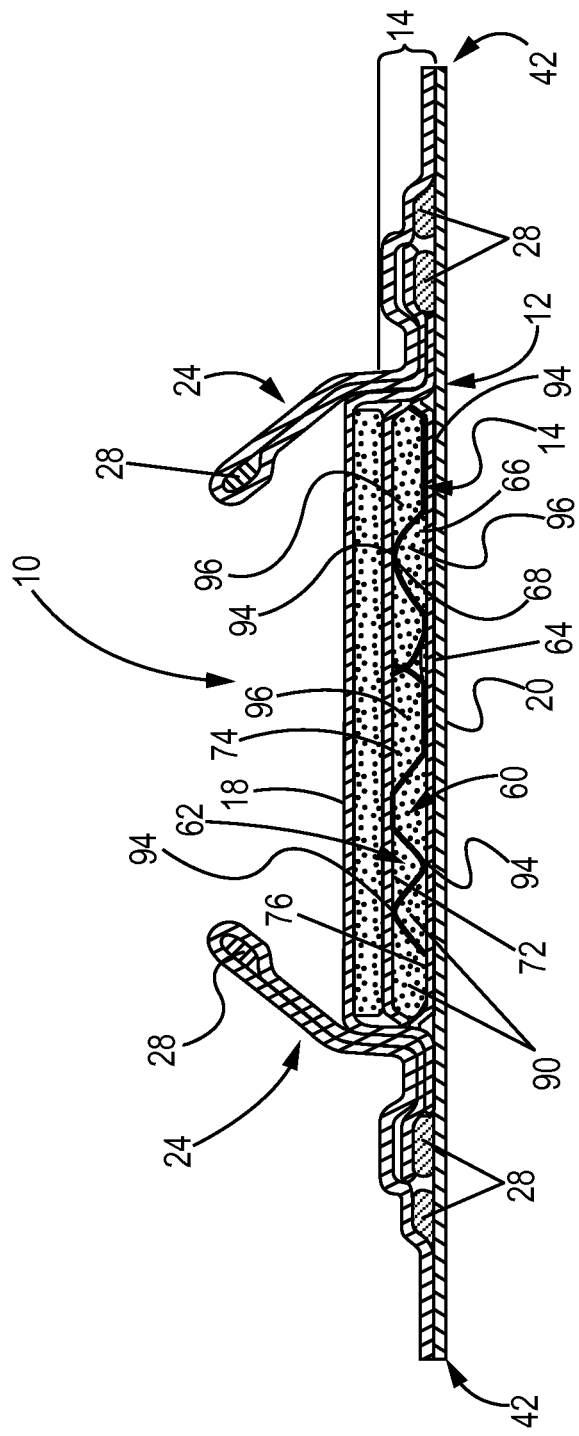

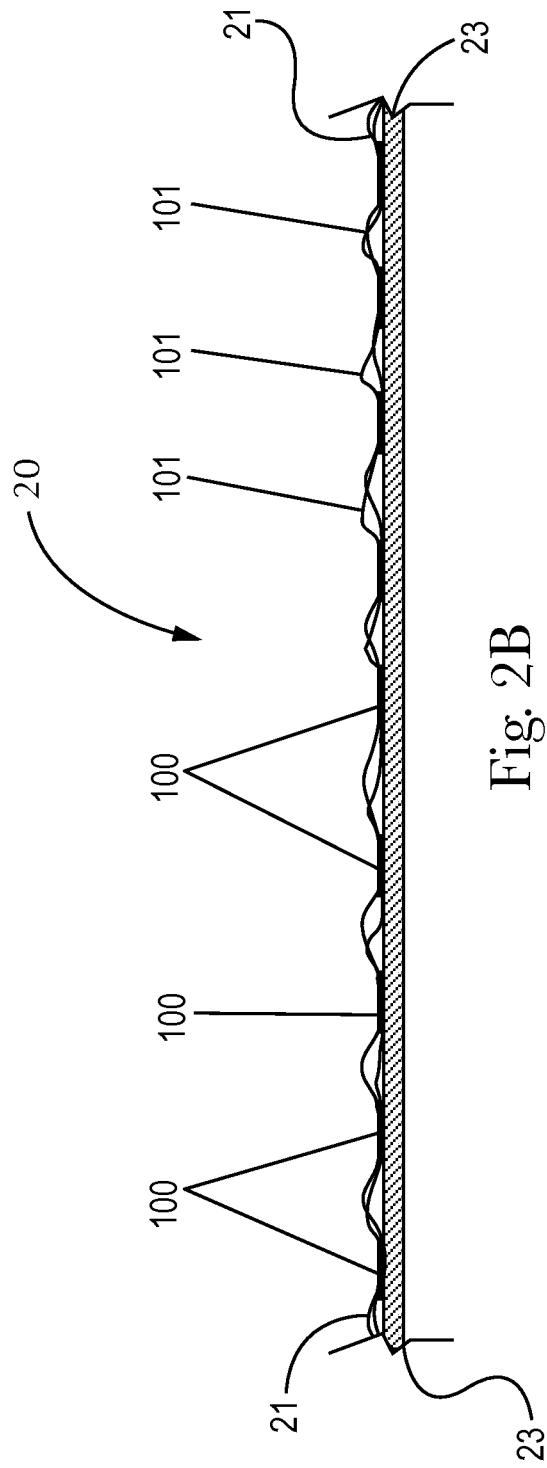

DIAPER STRUCTURE WITH ENHANCED TACTILE SOFTNESS ATTRIBUTES AND PROVIDING RELATIVELY LOW HUMIDITY

CROSS REFERENCE TO RELATED APPLICATION

This application is a continuation-in-part of, and claims priority under 35 U.S.C. § 120 to, U.S. patent application Ser. No. 13/953,772, filed on Jul. 30, 2013, which claims the benefit, under 35 U.S.C. § 119(e), of U.S. Provisional Patent Application Ser. No. 61/678,163, filed on Aug. 1, 2012, the entire disclosures of both are fully incorporated by reference herein.

BACKGROUND

The business of manufacturing and marketing disposable absorbent articles for personal care or hygiene (such as disposable diapers, training pants, adult incontinence undergarments, feminine hygiene products, breast pads, care mats, bibs, wound dressing products, and the like) is relatively capital intensive and highly competitive. To maintain or grow their market share and thereby maintain a successful business, manufacturers of such articles must continually strive to enhance their products in ways that serve to differentiate them from those of their competitors, while at the same time controlling costs so as to enable competitive pricing and the offering to the market of an attractive value-to-price proposition.

One way in which some manufacturers may seek to enhance such products is through enhancements to softness. Parents and caregivers naturally seek to provide as much comfort as they can for their babies, and utilizing products such as disposable diapers that they perceive as relatively soft provides reassurance that they are doing what they can to provide comfort in that context. With respect to other types of disposable absorbent articles that are designed to be applied and/or worn close to the skin, perceptions of softness can reassure the wearer or caregiver that the article will be comfortable. Thus, the manufacturer of such articles may devote efforts toward enhancing the softness attributes of the structure of an absorbent article and of the various materials used to make the absorbent article, including the outermost materials of the article (e.g. materials that are visible and/or exposed to the wearer's skin or touch).

It is believed that humans' perceptions of softness of an absorbent article can be affected by tactile signals, auditory signals, and visual signals.

Tactile softness signals may be affected by a variety of the article components' features and properties that have effect on its tactile feel. For example, many absorbent articles have outermost layer components formed of nonwoven materials, and attributes of such materials including but not limited to loft, fiber shape, thickness and density, basis weight, microscopic pliability and flexibility of individual fibers, macroscopic pliability and flexibility of the nonwoven web as formed by the fibers, surface friction characteristics, number of loose fibers or free fiber ends, and other features, may impact the tactile signals the absorbent article conveys.

Perceptions of softness also may be affected by auditory signals, e.g., whether and to what extent the materials of the absorbent article make audible rustling, crinkling or other noises when touched or manipulated.

It is believed that perceptions of softness of a material also may be affected by visual signals, i.e., its visual appearance. It is believed that, if materials forming an absorbent article look relatively soft to a person, it is much more likely that the person will perceive the absorbent article as having relative tactile softness as well. Visual impressions of softness may be affected by a variety of features and properties, including but not limited to color, opacity, light reflectivity, refractivity or absorption, apparent thickness/caliper, fiber size and density, and macroscopic physical surface features.

As a result of the complexity of the mix of the above-described characteristics and the subjective nature of individual perceptions, to the extent softness is considered an attribute of an absorbent article; it may elude precise measurement or quantification. Although several methods for measuring and evaluating material features that are believed to affect softness signals have been developed, there are no standard, universally accepted units or methods of measurement for softness. It is a subjective, relative concept, difficult to characterize in an objective way. Because softness is difficult to characterize, it can also be difficult to affect in a predictable way, through changes or adjustments to specifications in materials or manufacturing processes.

Complicating efforts to define and enhance softness is the fact that differing individuals will have differing individual physiological and experiential frames of reference and perceptions concerning what features and properties will cause them to perceive softness to a lesser or greater extent.

Various efforts have been made to provide or alter features of nonwoven web materials with the objective of enhancing loft and/or consumer perceptions of softness. These efforts have included selection and/or manipulation of fiber chemistry, basis weight, loft, fiber density, configuration and size, tinting and/or opacifying, embossing or bonding in various patterns, etc. Various approaches are described in, for example, co-pending U.S. application Ser. No. 13/428,404 by Xu et al.

Efforts at enhancing softness attributes and increasing perceptions of softness to date have had varying degrees of success, but have left room for improvements.

In addition, advancements to improve the level of softness of nonwoven materials have also usually increased the basis weight of the nonwoven materials. This increased basis weight, while increasing the softness level and often reducing physical skin irritation, may have a negative impact on the level of moisture at or near the skin. There remains a need for a diaper with soft materials on skin contacting surfaces to reduce physical skin irritation and also not negatively impact the relative humidity levels and moisture at or near the skin surface. There also remains a need for a diaper with soft materials on a garment-facing surface in combination with soft materials on the skin-contacting surface. There also remains a need for packages of absorbent articles comprising soft nonwoven materials having increased basis weights (e.g., 25 gsm or greater), but that provide low relative humidity levels at or near the skin surface, wherein the packages have a reduced in-bag stack height compared to conventional absorbent article packages so the packages are convenient for caregivers to handle and store and so that manufacturers enjoy low distribution costs.

SUMMARY

The present disclosure provides absorbent articles, such as disposable diapers, that are softer and less irritable to a wearer's skin compared to conventional absorbent articles. Softness can be increased by providing topsheets and, optionally, outermost layer or layers (not including the landing zone) of backsheets with high basis weights. The topsheets and the outermost layer or layers of backsheets may have a combined basis weight of at least 40 gsm, at least 45 gsm, or at least 50 gsm, for example. By providing softer topsheets and/or nonwoven materials of backsheets on absorbent articles, reduced physical skin irritation may occur during wear. Higher basis weight materials, however, may also retain more moisture in their corresponding larger filament structure. This may cause the high basis weight materials to retain more moisture at or near the skin, thereby impacting the hydration of the skin which may be a component to skin irritation. An absorbent article construction has been discovered to still deliver the reduction of physical skin irritation via high basis weight nonwovens, while also alleviating the relative moisture levels at or near the skin and with lower humidity within the absorbent article.

A form of the present disclosure provides an absorbent article comprising a high basis weight topsheet (e.g., greater than or equal to 25 gsm) that provides improved softness in combination with a substantially cellulose free, or cellulose free, absorbent core, which significantly reduces relative humidity within the absorbent article after one or more urination events. By reducing the amount of relative humidity produced by an absorbent article after one or more urination events, moisture on or near a wearer's skin may be significantly reduced, thereby leading to improved skin health and reduced skin irritation during the absorbent article wearing experience. It is believed the relative humidity within the absorbent article may be reduced because absorbent polymer material within the cellulose free, or substantially cellulose free, absorbent core obtains the urine and locks it in, with little to no vapor pressure contributed by typical airfelt or cellulose typically found in conventional absorbent cores. By providing an absorbent core that is free of or substantially free of cellulose fibers, moisture from urine can be inhibited from rising through the topsheet, as is the case when significant amounts of cellulose fiber (e.g., 40% cellulose by weight of the absorbent core) are present within a conventional absorbent core. The ability to remove moisture from the near skin environment enables the use of softer, higher basis weight materials against the wearer's skin without increasing skin irritation owing to moisture.

In a form, packages of the absorbent articles of the present disclosure are also provided that have a reduced in-bag stack height compared to conventional absorbent article packages regardless of the inclusion of high basis weight nonwoven webs. This reduced in-bag stack height of the packages allows caregivers to easily handle and store the packages while also providing manufacturers with reduced distribution costs.

In a form, a disposable diaper is provided. The diaper comprises a topsheet comprising a first nonwoven web. The topsheet may have a basis weight greater than or equal to about 25 gsm, greater than or equal to about 30 gsm, greater than or equal to about 35 gsm, greater than or equal to about 40 gsm, or greater than or equal to about 45 gsm, according to the Basis Weight Test herein. The diaper comprises a backsheet comprising a second nonwoven web and a film. The film may have a WVTR value of less than 6,500 g/m$^2$ day, according to the WVTR Test herein. The diaper comprises an absorbent core comprising an absorbent particulate polymer material disposed between the topsheet and the backsheet. The absorbent core may be substantially cellulose free or cellulose free. The diaper may have a relative humidity of less than 75%, of less than 74%, of less than 73%, of less than 70%, or of less than 65%, according to the Humidity Test herein.

In a form, a disposable diaper comprises a topsheet comprising a first nonwoven web and a backsheet comprising a second nonwoven web and a film. The second nonwoven web forms a portion of an outermost layer of the diaper. The film may have a WVTR value of less than 6,500 g/m$^2$ day, according to the WVTR Test herein. The diaper comprises an absorbent core comprising an absorbent particulate polymer material disposed between the topsheet and the outermost layer. The absorbent core may be substantially cellulose free or cellulose free. The first nonwoven web and the second nonwoven web may have a combined basis weight of at least 40 gsm, at least 45 gsm, or at least 50 gsm, according to the Basis Weight Test herein. The disposable diaper may have a relative humidity of less than 72%, less than 70%, or less than 68%, according to the Humidity Test herein.

In a form, a disposable diaper comprises an innermost layer comprising a first nonwoven web and an outermost layer comprising a second nonwoven web and a film. The film may have a WVTR value of less than 6,000 g/m$^2$ day, according to the WVTR Test herein. The diaper may comprise a substantially cellulose free, or cellulose free, absorbent core positioned between the innermost layer and the outermost layer. The substantially cellulose free, or cellulose free, absorbent core may comprise a first substrate, a second substrate, a thermoplastic adhesive material, and an absorbent particulate polymer material. The thermoplastic adhesive material and the absorbent particulate polymer material may be positioned intermediate the first and second substrates. The first nonwoven web and the second nonwoven web have a combined basis weight of at least 40 gsm, at least 45 gsm, or at least 50 gsm, according to the Basis Weight Test herein. The disposable diaper may have a relative humidity of less than 75%, of less than 74%, of less than 73%, of less than 70%, or of less than 65%, according to the Humidity Test herein.

BRIEF DESCRIPTION OF THE DRAWINGS

FIG. 2A is a cross section of the diaper depicted in FIGS. 1A and 1B, taken through line 2-2 in those figures;

FIG. 2B is a schematic cross section of a portion of a laminate of a polymeric film and a nonwoven web, taken through a pattern of bond impressions in the nonwoven web;

DETAILED DESCRIPTION

Definitions

Figure 1A:
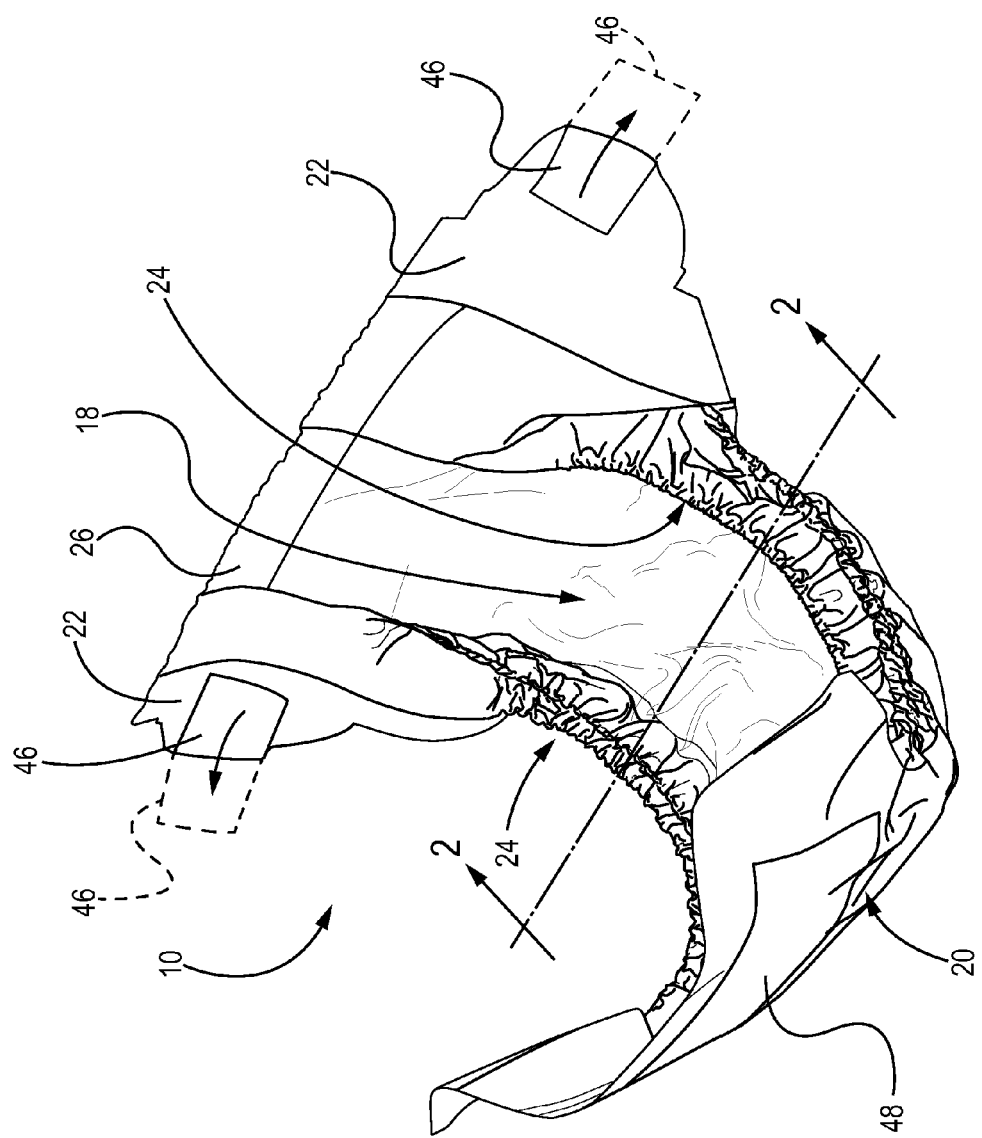
FIG. 1A is a perspective view of a disposable diaper shown laid out horizontally in a relaxed condition, wearer-facing surfaces up.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments and pads, feminine hygiene pads, breast pads, care mats, bibs, wound dressing products, and the like. As used herein, the term "exudates" includes, but is not limited to, urine, blood, vaginal discharges, and fecal matter.

"Absorbent core" means a structure typically disposed between a topsheet and backsheet of an absorbent article for absorbing and containing liquid received by the absorbent article. The absorbent core may also include a cover layer or envelope. The cover layer or envelope may comprise a nonwoven. In some examples, the absorbent core may include one or more substrates, an absorbent polymer material, and a thermoplastic adhesive material/composition adhering and immobilizing the absorbent polymer material to a substrate, and optionally a cover layer or envelope.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

"Absorbent particulate polymer material area" as used herein refers to the area of the core wherein the first substrate and second substrate are separated by a multiplicity of superabsorbent particles. There may be some extraneous superabsorbent particles outside of this area between the first substrate 64 and second substrate.

"Airfelt" is used herein to refer to comminuted wood pulp, which is a form of cellulosic fiber.

A "batt" is used herein to refer to fiber materials prior to being consolidated in a final calendering process as described herein. A "batt" comprises individual fibers, which are usually unbonded to each other, although a certain amount of pre-bonding between fibers may be performed and is also included in the meaning, such as may occur during or shortly after the lay-down of fibers in a spunlaying process, or as may be achieved be a pre-calendering. This pre-bonding, however, still permits a substantial number of the fibers to be freely moveable such that they can be repositioned. A "batt" may comprise several strata, such as may result from depositing fibers from several beams in a spunlaying process.

"Bicomponent" refers to fiber having a cross-section comprising two discrete polymer components, two discrete blends of polymer components, or one discrete polymer component and one discrete blend of polymer components. "Bicomponent fiber" is encompassed within the term "multicomponent fiber." A Bicomponent fiber may have an overall cross section divided into two or more subsections of the differing components of any shape or arrangement, including, for example, coaxial subsections, core-and-sheath subsections, side-by-side subsections, radial subsections, etc.

"Bond area percentage" on a nonwoven web is a ratio of area occupied by bond impressions, to the total surface area of the web, expressed as a percentage, and measured according to the Bond Area Percentage Method set forth herein.

"Bonding roller," "calender roller" and "roller" are used interchangeably.

A "bond impression" in a nonwoven web is the surface structure created by the impression of a bonding protrusion on a calender roller into a nonwoven web. A bond impression is a location of deformed, intermeshed or entangled, and melted or thermally fused, materials from fibers superimposed and compressed in a z-direction beneath the bonding protrusion, which form a bond. The individual bonds may be connected in the nonwoven structure by loose fibres between them. The shape and size of the bond impression approximately corresponds to the shape and size of the bonding surface of a bonding protrusion on the calender roller.

"Cellulose free" is used herein to describe a portion of an article, such as an absorbent core, that contains no cellulosic fibers by weight of the absorbent material within the absorbent core. Cellulose free is also used herein to describe an acquisition/distribution system that contains no cellulosic fibers by weight of the acquisition/distribution system.

A "column" of bonds on a nonwoven web is a group of nearest neighboring bonds of like shape and rotational orientation that are arranged along the line that extends most predominately in the machine direction.

"Cross direction" (CD)—with respect to the making of a nonwoven web material and the nonwoven web material, refers to the direction along the web material substantially perpendicular to the direction of forward travel of the web material through the manufacturing line in which the web material is manufactured. With respect to a batt moving through the nip of a pair of calender rollers to form a bonded nonwoven web, the cross direction is perpendicular to the direction of movement through the nip, and parallel to the nip.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants, toddlers, children, and adult incontinent persons about the lower torso so as to encircle the waist and legs of the wearer and that is specifically adapted to receive and contain urinary, menses, and fecal waste. As used herein, term "diaper" also includes "pant" which is defined below.

"Fiber" and "filament" are used interchangeably.

"Fiber diameter" is expressed in units of μm. The terms "grams of fiber per 9000 m" (denier or den) or "grams of fiber per 10000 m" (dTex) are used to describe the fineness or coarseness of fibers, which are linked to the diameter (when assumed to be circular) by the density of the employed material(s).

"Film"—means a skin-like or membrane-like layer of material formed of one or more polymers, which does not have a form consisting predominately of a web-like structure of consolidated polymer fibers and/or other fibers.

"Length" or a form thereof, with respect to a diaper or training pant, refers to a dimension measured along a direction perpendicular to the waist edges and/or parallel to the longitudinal axis.

"Machine direction" (MD)—with respect to the making of a nonwoven web material and the nonwoven web material, refers to the direction along the web material substantially parallel to the direction of forward travel of the web material through the manufacturing line in which the web material is manufactured. With respect to a nonwoven batt moving through the nip of a pair of calender rollers to form a bonded nonwoven web, the machine direction is parallel to the direction of movement through the nip, and perpendicular to the nip.

"Monocomponent" refers to fiber formed of a single polymer component or single blend of polymer components, as distinguished from bicomponent or multicomponent fiber.

"Multicomponent" refers to fiber having a cross-section comprising more than one discrete polymer component, more than one discrete blend of polymer components, or at least one discrete polymer component and at least one discrete blend of polymer components. "Multicomponent fiber" includes, but is not limited to, "bicomponent fiber." A multicomponent fiber may have an overall cross section divided into subsections of the differing components of any shape or arrangement, including, for example, coaxial subsections, core-and-sheath subsections, side-by-side subsections, radial subsections, islands-in-the-sea, etc.

A "nonwoven" is a manufactured sheet or web of directionally or randomly oriented fibers which are first formed into a batt and then consolidated and bonded together by friction, cohesion, adhesion or one or more patterns of bonds and bond impressions created through localized compression and/or application of pressure, heat, ultrasonic or heating energy, or a combination thereof. The term does not include fabrics which are woven, knitted, or stitch-bonded with yarns or filaments. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes including but not limited to meltblowing, spunbonding, spunmelting, solvent spinning, electrospinning, carding, film fibrillation, melt-film fibrillation, airlaying, dry-laying, wetlaying with staple fibers, and combinations of these processes as known in the art. The basis weight of nonwoven fabrics is usually expressed in grams per square meter (gsm).

"Opacity" is a numeric value relating to the ability of a web material to transmit light therethrough, measured according the Opacity Measurement Method set forth herein.

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al. on Sep. 28, 1999.

When used as an adjective in connection with a component of a material, the term "predominately" means that the component makes up greater than 50% by weight of the material. When used as an adjective in connection with a directional orientation of a physical feature or geometric attribute thereof, "predominately" means the feature or attribute has a projection onto a line extending along the direction indicated, greater in length than the projection onto a line perpendicular thereto. Within other contexts, the term "predominantly" refers to a condition which imparts a substantial effect on a property or feature. Thus, when a material comprises "predominantly" a component said to impart a property, this component imparts a property that the material otherwise would not exhibit. For example, if a material comprises "predominantly" heat-fusible fibers, the quantity and components of these fibers must be sufficient to allow heat fusion of the fibers.

A "bonding protrusion" or "protrusion" is a feature of a bonding roller at its radially outermost portion, surrounded by recessed areas. Relative the rotational axis of the bonding roller, a bonding protrusion has a radially outermost bonding surface with a bonding surface shape and a bonding surface shape area, which generally lies along an outer cylindrical surface with a substantially constant radius from the bonding roller rotational axis; however, protrusions having bonding surfaces of discrete and separate shapes are often small enough relative the radius of the bonding roller that the bonding surface may appear flat/planar; and the bonding surface shape area is closely approximated by a planar area of the same shape. A bonding protrusion may have sides that are perpendicular to the bonding surface, although usually the sides have an angled slope, such that the cross section of the base of a bonding protrusion is larger than its bonding surface. A plurality of bonding protrusions may be arranged on a calender roller in a pattern. The plurality of bonding protrusions has a bonding area per unit surface area of the outer cylindrical surface which can be expressed as a percentage, and is the ratio of the combined total of the bonding shape areas of the protrusions within the unit, to the total surface area of the unit.

A "row" of bonds on a nonwoven web is a group of nearest neighboring bonds of like shape and rotational orientation that are arranged along the line that extends most predominately in the cross direction.

"Substantially cellulose free" is used herein to describe a portion of an article, such as an absorbent core, that contains less than 10% by weight cellulosic fibers, less than 5% cellulosic fibers, less than 3% cellulosic fibers, less than 2% cellulosic fibers, less than 1% cellulosic fibers, or no more than an immaterial amount of cellulosic fibers by weight of the absorbent material within the absorbent core. An immaterial amount of cellulosic material would not materially affect the thinness, flexibility, or absorbency of an absorbent core. Substantially cellulose free is also be used herein to describe an acquisition/distribution system with the same amounts of cellulosic fibers specified above, by weight of the acquisition/distribution system.

"Substantially continuously distributed" as used herein indicates that within the absorbent particulate polymer material area, the first substrate 64 and second substrate 72 are separated by a multiplicity of superabsorbent particles. It is recognized that there may be minor incidental contact areas between the first substrate 64 and second substrate 72 within the absorbent particulate polymer material area. Incidental contact areas between the first substrate 64 and second substrate 72 may be intentional or unintentional (e.g. manufacturing artifacts) but do not form geometries such as pillows, pockets, tubes, and the like.

"Tensile Strength" refers to the maximum tensile force (Peak Force) a material will sustain before tensile failure, as measured by the Tensile Strength Measurement Method set forth herein.

"Thickness" and "caliper" are used herein interchangeably.

"Total Stiffness" refers to the measured and calculated value relating to a material, according to the Stiffness measurement method set forth herein.

"Density" is the ratio of basis weight and thickness and indicates the bulkiness and fluffiness of the product, which are important properties of the nonwoven web according to the present disclosure. The lower the value, the bulkier is the web.

Density $[kg/m^3]$=basis weight $[g/m^2]$/thickness [mm].

"Width" or a form thereof, with respect to a diaper or training pant, refers to a dimension measured along a direction parallel to the waist edges and/or perpendicular to the longitudinal axis.

"Z-direction," with respect to a web, means generally orthogonal or perpendicular to the plane approximated by the web along the machine and cross direction dimensions.

DESCRIPTION

Examples of the present disclosure include disposable absorbent articles having improved softness attributes.

Figure 1B:
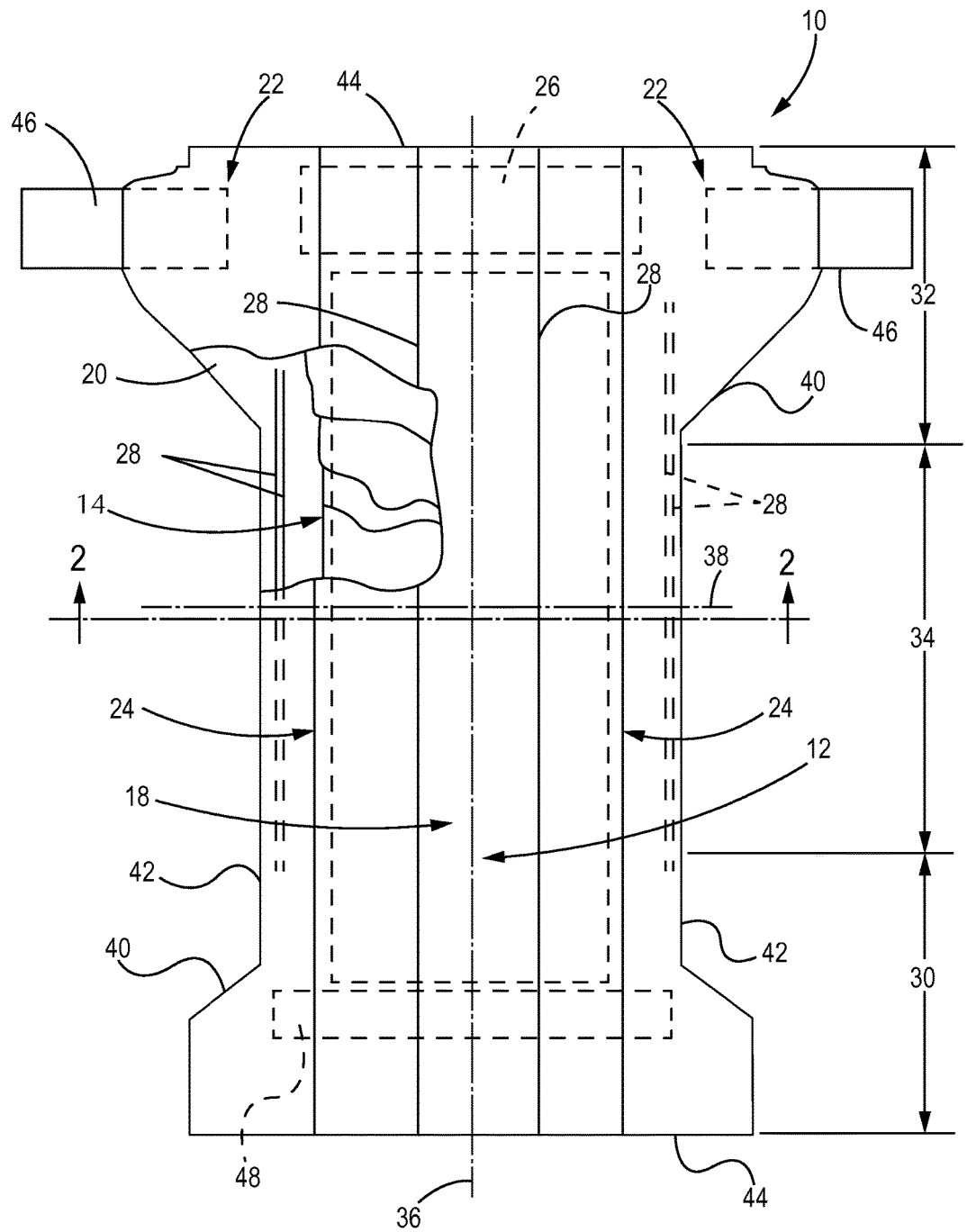
FIG. 1B is a plan view of a disposable diaper shown laid out horizontally in a stretched out, flattened state (stretched out against elastic contraction induced by the presence of elastic members), wearer-facing surfaces facing the viewer.

FIG. 1A is a perspective view of a diaper 10 in a relaxed, laid-open position as it might appear opened and lying on a horizontal surface. FIG. 1B is a plan view of a diaper 10 shown in a flat-out, uncontracted state (i.e., without elastic induced contraction), shown with portions of the diaper 10 cut away to show underlying structure. The diaper 10 is depicted in FIG. 1B with its longitudinal axis 36 and its lateral axis 38. Portions of the diaper 10 that contact a wearer are shown oriented upwards in FIG. 1A, and are shown facing the viewer in FIG. 1B. FIG. 2A is a cross section of the diaper taken at line 2-2 in FIG. 1B.

The diaper 10 generally may comprise a chassis 12 and an absorbent core 14 disposed in the chassis. The chassis 12 may comprise the main body of the diaper 10.

The chassis 12 may include a topsheet 18, which may be liquid pervious, and a backsheet 20, which may be liquid impervious. The absorbent core 14 may be encased between the topsheet 18 and the backsheet 20. The chassis 12 may also include side panels 22, elasticized leg cuffs 24, and an elastic waist feature 26. The chassis 12 may also comprise a fastening system, which may include at least one fastening member 46 and at least one landing zone 48. One or more layers of the topsheet and/or backsheet may be formed of a nonwoven web as described below.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The crotch region 34 may include from 33.3% to 50% of the overall length of the diaper 10, and each of waist regions 30, 32 may correspondingly include from 25% to 33.3% of the overall length of the diaper 10.

The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 may also include such other features including front and rear ear panels, waist cap features, elastics and the like to provide better fit, containment and aesthetic characteristics. Such additional features are described in, e.g., U.S. Pat. Nos. 3,860,003 and 5,151,092.

In order to apply and keep diaper 10 in place about a wearer, the second waist region 32 may be attached by the fastening member 46 to the first waist region 30 to form leg opening(s) and an article waist. When fastened, the fastening system carries a tensile load around the article waist.

According to some examples, the diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, stretch laminates, activated stretch laminates, fiber reinforced plastics and the like, or combinations thereof. In some examples, the materials making up the fastening device may be flexible. In some examples, the fastening device may comprise cotton or cotton-like materials for additional softness or consumer perception of softness. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the topsheet 18, the backsheet 20, and the absorbent core 14 may be assembled in a variety of well-known configurations, some diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 18 may be fully or partially elasticized and/or may be foreshortened to create a void space between the topsheet 18 and the absorbent core 14. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The topsheet may comprise one or more layers. The layers may be bonded, hydroentangled (such as disclosed in U.S. Pat. Appl., Publ. No. 2014/0121621), adhesively joined, or otherwise joined.

The backsheet 20 may be joined with the topsheet 18. The backsheet 20 may serve to prevent the exudates absorbed by the absorbent core 14 and contained within the diaper 10 from soiling other external articles that may contact the diaper 10, such as bed sheets and clothing. Referring to FIG. 2B, the backsheet 20 may be substantially impervious to liquids (e.g., urine) and may be formed of a laminate of a nonwoven 21 and a thin polymeric film 23 such as a thermoplastic film having a thickness of about 0.012 mm (0.5 mil) to about 0.051 mm (2.0 mils). The backsheet films may have the WVTR values set forth herein, according to the WVTR Test. Nonwoven 21 may be a nonwoven web as described herein. Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 20. Exemplary breathable materials may include materials such as woven webs, nonwoven webs, composite materials such as film-coated nonwoven webs, and microporous films such as manufactured by Mitsui Toatsu Co., of Japan under the designation ESPOIR and by EXXON Chemical Co., of Bay City, Tex., under the designation EXXAIRE. Suitable breathable composite materials comprising polymer blends are available from Clopay Corporation, Cincinnati, Ohio under the name HYTREL blend Pl 8-3097. Other examples of such breathable composite materials are described in greater detail in PCT Application No. WO 95/16746, published on Jun. 22, 1995 in the name of E. I. DuPont. Other breathable backsheets including nonwoven webs and apertured formed films are described in U.S. Pat. No. 5,571,096 issued to Dobrin et al. on Nov. 5, 1996.

The diaper 10 may comprise an acquisition/distribution system. The acquisition/distribution system may have one or more layers of the same or different materials. The acquisition/distribution system may comprise one layer comprising at least 50% by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf). The cross-linked cellulosic fibers provide higher resilience and, therefore, higher resistance to the first absorbent layer against the compression in the product packaging or in use conditions, e.g., under baby weight. This provides the core with a higher void volume, permeability, and liquid absorption, and hence reduced leakage and improved dryness.

The acquisition/distribution system may be positioned intermediate the topsheet and the absorbent core and/or may be positioned intermediate the backsheet and the absorbent core.

Example chemically cross-linked cellulosic fibers suitable for a distribution layer are disclosed in U.S. Pat. No. 5,549,791, U.S. Pat. No. 5,137,537, WO 9534329, and U.S. Pat. App. Publ. No. 2007/118087. Example cross-linking agents include polycarboxylic acids such as citric acid and/or polyacrylic acids, such as acrylic acid and maleic acid copolymers.

The layer of the acquisition/distribution system comprising cross-linked cellulose fibers may comprise other fibers, but this layer may advantageously comprise at least 50%, at least 60%, at least 70%, at least 80%, at least 90%, or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

The layer of the acquisition/distribution system comprising the cross-linked cellulose fibers may typically have an average basis weight of from about 25 gsm to about 400 gsm, from about 40 gsm to about 300 gsm, greater than about 30 gsm, greater than about 40 gsm, or greater than about 50 gsm, specifically reciting all 1.0 gsm increments within the above-specified ranges and any ranges formed therein or thereby. This layer may also have a total mass of greater than about 1 gram, greater than about 2 grams, or greater than about 3 grams.

The acquisition/distribution system may also comprise a layer comprising a nonwoven material, such as an SMS material or an SMMS material, comprising a spunbonded, a high-loft nonwoven web, a nonwoven web, a melt-blown, a hydroentangled web, a carded nonwoven, a thermally bonded carded nonwoven, and a further spunbonded layer or alternatively a carded chemical-bonded nonwoven. In some forms, this layer may comprise air-laid or wet-laid cellulosic, cross-linked cellulosic, or synthetic fibers, conjugate fibers, bicomponent fibers, staple fibers, rayon fibers, or blends thereof.

The layer of the acquisition/distribution system comprising the nonwoven material may typically have an average basis weight of from about 30 gsm to about 400 gsm, from about 40 gsm to about 300 gsm, greater than about 30 gsm, greater than about 40 gsm, or greater than about 50 gsm, specifically reciting all 1.0 gsm increments within the above-specified ranges and any ranges formed therein or thereby.

The acquisition/distribution system may be substantially cellulose free, or cellulose free, by weight of the acquisition/distribution system. In other instances, the acquisition/distribution system may comprise no more than an immaterial amount of cellulose fibers.

Suitable nonwoven web materials useful in the present disclosure include, but are not limited to spunbond, melt-blown, spunmelt, solvent-spun, electrospun, carded, film fibrillated, melt-film fibrillated, air-laid, dry-laid, wet-laid staple fibers, and other and other nonwoven web materials formed in part or in whole of polymer fibers, as known in the art. A suitable nonwoven web material may also be an SMS material, comprising a spunbonded, a melt-blown and a further spunbonded stratum or layer or any other combination of spunbonded and melt-blown layers, such as a SMMS or SSMMS etc. Examples include one or more layers of fibers with diameters below 1 micron (nanofibers and nanofiber layers); examples of these rise in combinations of SMS, SMNS, SSMNS or SMNMS nonwoven webs (where "N" designates a nanofiber layer). In some examples, permanently hydrophilic nonwovens, and in particular, nonwovens with durably hydrophilic coatings may be desirable. Typically, the suitable non-woven is air permeable. Typically the suitable nonwoven is water or liquid permeable, but may also be water impermeable by reason of fiber size and density, and hydrophobicity of the fibers. Water or liquid permeability may be enhanced by treatments to render the fibers hydrophilic, as discussed below.

The nonwoven web may be formed predominately of polymeric fibers. In some examples, suitable non-woven fiber materials may include, but are not limited to polymeric materials such as polyolefins, polyesters, polyamide, or specifically polypropylene (PP), polyethylene (PE), poly-lactic acid (PLA), polyethylene terephthalate (PET) and/or blends thereof. Nonwoven fibers may be formed of, or may include as additives or modifiers, components such as aliphatic polyesters, thermoplastic polysaccharides, or other biopolymers (bio-based or renewable polymers).

The individual fibers may be monocomponent or multicomponent. The multicomponent fibers may be bicomponent, such as in a core-and-sheath or side-by-side arrangement. Often, the individual components comprise aliphatic polyolefins such as polypropylene or polyethylene, or their copolymers, aliphatic polyesters, thermoplastic polysaccharides or other biopolymers.

Further useful nonwovens, fiber compositions, formations of fibers and nonwovens and related methods are described in U.S. Pat. No. 6,645,569 to Cramer et al., U.S. Pat. No. 6,863,933 to Cramer et al., U.S. Pat. No. 7,112,621 to Rohrbaugh et al.; co-pending U.S. patent application Ser. Nos. 10/338,603 and 10/338,610 by Cramer et al., and Ser. No. 13/005,237 by Lu et al., the disclosures of which are incorporated by reference herein.

Some polymers used for nonwoven fiber production may be inherently hydrophobic, and for certain applications they may be surface treated or coated with various agents to render them hydrophilic. A surface coating may include a surfactant coating. One such surfactant coating is available from Schill & Silacher GmbH, Böblingen, Germany, under the Tradename Silastol PHP 90.

Another way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720.

Another way to produce hydrophilic nonwovens made predominantly from hydrophobic polymers such as polyolefins is to add hydrophilic additives into the melt prior to extrusion.

Another way to produce nonwovens with durably hydrophilic coatings is to coat the nonwoven with hydrophilic nanoparticles as described in co-pending application U.S. Pat. No. 7,112,621 to Rohrbaugh et al. and in PCT Application Publication WO 02/064877.

Typically, nanoparticles have a largest dimension of below 750 nm. Nanoparticles with sizes ranging from 2 to 750 nm may be economically produced. An advantage of nanoparticles is that many of them can be easily dispersed in water solution to enable coating application onto the nonwoven, they typically form transparent coatings, and the coatings applied from water solutions are typically sufficiently durable to exposure to water. Nanoparticles can be organic or inorganic, synthetic or natural. Inorganic nanoparticles generally exist as oxides, silicates, and/or carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to one example, a suitable nanoparticle coated non-woven is that disclosed in the co-pending patent application Ser. No. 10/758,066 entitled "Disposable absorbent article comprising a durable hydrophilic core wrap" by Ponomarenko and Schmidt.

In some cases, the nonwoven web surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, hydrophilic nonwovens are also useful in other parts of an absorbent article. For example, topsheets and absorbent core layers comprising permanently hydrophilic nonwovens as described above have been found to work well.

A nonwoven also may include other types of surface coating. In one example, the surface coating may include a fiber surface modifying agent that reduces surface friction and enhances tactile lubricity. Example fiber surface modifying agents are described in U.S. Pat. Nos. 6,632,385 and 6,803,103; and U.S. Pat. App. Pub. No. 2006/0057921.

According to one example, the nonwoven may comprise a material that provides good recovery when external pressure is applied and removed. Further, according to one example, the nonwoven may comprise a blend of different fibers selected, for example from the types of polymeric fibers described above. In some embodiments, at least a portion of the fibers may exhibit a spiral curl which has a helical shape. According to one example, the fibers may include bicomponent fibers, which are individual fibers each comprising different materials, usually a first and a second polymeric material. It is believed that the use of side-by-side bi-component fibers is beneficial for imparting a spiral curl to the fibers.

In order to enhance softness perceptions of the absorbent article, nonwovens forming the backsheet may be hydroenhanced or hydroengorged. Hydroenhanced/hydroengorged nonwovens are described in U.S. Pat. Nos. 6,632,385 and 6,803,103, and U.S. Pat. App. Pub. No. 2006/0057921, the disclosures of which are incorporated herein by reference.

A nonwoven may also be treated by a "selfing" mechanism. By "selfing" nonwovens, high densities of loops (>150 in 2) may be formed which protrude from the surface of the nonwoven substrate. Since these loops act as small flexible brushes, they create an additional layer of springy loft, which may enhance softness. Nonwovens treated by a selfing mechanism are described in U.S. Pat. App. Pub. No. US 2004/0131820.

Any of the nonwoven types described herein may be used for the topsheet, backsheet outer layer, loops component in a hook-and-loop fastening system of an absorbent article, or any other portion of a manufactured article such as cleansing wipes and other personal hygiene products, dusters and dusting cloths, household cleaning cloths and wipes, laundry bags, dryer bags and sheets comprising a layer formed of nonwoven web.

The absorbent core generally may be disposed between the topsheet 18 and the backsheet 20. It may include one or more layers, such as a first absorbent layer 60 and a second absorbent layer 62.

The absorbent layers 60, 62 may include respective substrates 64, 72, an absorbent particulate polymer material 66, 74 disposed on substrates 64, 72, and a thermoplastic adhesive material 68, 76 disposed on and/or within the absorbent particulate polymer material 66, 74 and at least portions of the substrates 64, 72 as an adhesive for immobilizing the absorbent particulate polymer material 66, 74 on the substrates 64, 65.

The substrate 64 of the first absorbent layer 60 may be referred to as a dusting layer and has a first surface which faces the backsheet 20 and a second surface which faces the absorbent particulate polymer material 66. Likewise, the substrate 72 of the second absorbent layer 62 may be referred to as a core cover and has a first surface facing the topsheet 18 and a second surface facing the absorbent particulate polymer material 74.

The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

The substrates 64, 72 may be of one or more nonwoven materials, and may be liquid permeable.

As illustrated in FIG. 2A, the absorbent particulate polymer material 66, 74 may be deposited on the respective substrates 64, 72 in clusters 90 of particles to form a grid pattern comprising land areas 94 and junction areas 96 between the land areas 94. Land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 96 in the grid pattern contain little or no absorbent particulate polymer material 66 and 74. The land areas 94 and junction areas 96 can have a variety of shapes including, but not limited to, circular, oval, square, rectangular, triangular, and the like. First and second layers 60, 62 may be combined to form the absorbent core 14. Examples of suitable absorbent articles and cores are described in U.S. application Ser. No. 12/141,122; U.S. Pat. Nos. 7,744,576 and 7,750,203; and PCT Pub. No. WO 2009/060384, which describe core structures having a relatively low quantity of cellulosic fibers (e.g. less than 40% of the combined weight of cellulose fibers and absorbent polymer material), or are even substantially cellulose-free.

Signal ingredients may be incorporated into one or more components of the absorbent article. Signal ingredients may include, but are not limited to, vitamins A, E, D, and C, panthenol, niacin, omega 3 oils, cocoa butter, beeswax, cashmere, sweet almond oil, jojoba, oatmeal, aloe, cotton, honey, and silk. These signal ingredients may be added to an absorbent article for the purpose of signaling a benefit to the consumer. As an example, one or more of these signal ingredients may be added to a lotion that may be applied to an absorbent article component. The signal ingredient alone, or in a lotion, may be applied to the topsheet, backsheet, or any other component of the absorbent article. The lotion may comprise less than about 0.1% by weight, less than about 0.01% by weight, less than about 0.006% by weight, less than about 0.005% by weight, less than about 0.004% by weight, less than about 0.003% by weight, less than about 0.002% by weight, and less than about 0.001% by weight of the signal ingredient.

Additionally, a signal ingredient may, in combination with other absorbent article features, result in an unexpected synergy for communicating a benefit to the consumer. As an example, consumers may respond unexpectedly more favorably to an absorbent article that is thin and perceptibly soft in combination with a communication that lotion in the diaper comprises vitamin E than they would respond to either communication on its own.

An example of a diaper lotion comprising vitamin E as a signal ingredient may include the following formula: PET/StOH Mix (ratio=1.41) 94.0% to 99.8% (by weight) Aloe Extract 0.1% to 3.0% (by weight) Vitamin E 0.001% to 0.1% (by weight). Further, vitamin E may be used in its natural form or esters of natural vitamin E may be used (e.g., vitamin E acetate). U.S. App. Pub. Nos. 2002/0143304; 2004/0175343; 2003/0077307; U.S. Pat. Nos. 5,643,588; 5,635,191; 5,607,760; 6,861,571; and PCT Application Nos. WO 00/69481; and WO 98/24391 disclose various absorbent article lotions that signal ingredients may be added to.

The foregoing description describes features of an absorbent article, any combination of which can be employed to enhance consumer perceptions of softness of the article. In addition, however, it is believed that manufacturing a nonwoven web, and using it as a component of an absorbent article including, e.g., a topsheet 18 and/or backsheet 20 (see FIGS. 2A, 2B), according to the following description, provides for enhancement of loft of the component, and has synergistic effects with respect to enhancing perceptions of softness of the article as a whole. At the same time, counterintuitively, features described below may enhance tensile strength of the nonwoven web, and consequently, of the topsheet, backsheet or other component formed of it. When attempting to improve softness signals, preserving or enhancing tensile strength of a nonwoven may be of particular interest in absorbent articles for at least two reasons. First, the nonwoven web may typically be required to sustain certain minimum tensile forces and undergo sufficiently low changes in dimension so as to be effectively processable in downstream manufacturing operations. Second, the nonwoven web typically may be a substantial contributor to structural integrity of a the manufactured product, such as a disposable diaper, in which the backsheet may be required to sustain forces resulting from application/donning on a wearer (e.g., when a caregiver tugs on fastening members to apply a diaper), wearer movements, and weight and bulk contained and sustained by the backsheet when the diaper is loaded with the wearer's exudates.

As previously noted, referring to FIG. 2B, a backsheet 20 may be formed of a laminate of a nonwoven 21 and a thin polymeric film 23. The nonwoven and film may be bonded in the laminating process by adhesive or any other suitable means. In some examples, the polymeric film may have a thickness of about 0.012 mm (0.5 mil) to about 0.051 mm (2.0 mils). In order to achieve the desired overall visual appearance, the opacity and whiteness of the backsheet laminate may be enhanced by addition of, for example, calcium carbonate ($CaCO_3$) to the film during its formation. Inclusion of fine particles of $CaCO_3$ cause the formation of micropores about the particles upon stretching, or biaxial stretching in processing of the film, which serve to make the resulting film air- and vapor-permeable (thus, "breathable", reducing the likelihood of skin overhydration and thereby reducing the likelihood of conditions such as diaper rash). The $CaCO_3$ particles and the resulting micropores in the film also serve to enhance its opacity. Examples of suitable films include MICROPRO microporous films, and films designated BR137P and BR137U, available from Clopay Corporation, Mason, Ohio. In some examples, the polymeric film may be formed of components, and as described, in U.S. Patent Application Pub. No. 2008/0306463, and may include some or all of the features and/or components described therein, that reduce the film's vulnerability to glue "burn-through."

The nonwoven 21 may be formed from one or more resins of polyolefins, polyesters, polyamide including but not limited to polypropylene (PP), polyethylene (PE), and polyethylene terephthalate (PET), poly-lactic acid (PLA), and blends thereof. Resins including polypropylene may be particularly useful because of polypropylene's relatively low cost and surface friction properties of fibers formed from it (i.e., they have a relatively smooth, slippery tactile feel). Resins including polyethylene may also be desirable because of polyethylene's relative softness/pliability and even more smooth/slippery surface friction properties. Relative each other, PP currently has a lower cost and fibers formed from it have a greater tensile strength, while PE currently has a greater cost and fibers formed from it have a lower tensile strength but greater pliability and a more smooth/slippery feel. Accordingly, it may be desirable to form nonwoven web fibers from a blend of PP and PE resins, finding a balance of the best proportions of the polymers to balance their advantages and disadvantages. In some examples, the fibers may be formed of PP/PE blends such as described in U.S. Pat. No. 5,266,392. Nonwoven fibers may be formed of, or may include as additives or modifiers, components such as aliphatic polyesters, thermoplastic polysaccharides, or other biopolymers.

The individual fibers may be monocomponent or multicomponent. The multicomponent fibers may be bicomponent, such as in a core-and-sheath or side-by-side arrangement. Often, the individual components comprise aliphatic polyolefins such as polypropylene or polyethylene, or their copolymers, aliphatic polyesters, thermoplastic polysaccharides or other biopolymers.

A batt may be formed from any of these resins by conventional methods, such as carding, meltblowing, spunlaying, airlaying, wet-laying etc. An execution relates to spunbonding processes, in which the resin(s) are heated and forced under pressure through spinnerets. The spinnerets eject fibers of the polymer(s), which are then directed onto a moving belt; as they strike the moving belt they may be laid down in somewhat random orientations, but often with a machine-direction orientation or bias, to form a spunlaid batt. The batt then may be calender-bonded to form the nonwoven web.

Nonwovens formed of any basis weight may be used. However, as noted in the background, relatively higher basis weight, while having relatively greater apparent caliper and loft, also has relatively greater cost. On the other hand, relatively lower basis weight, while having relatively lower cost, adds to the difficulty of providing a nonwoven that provides superior tactile experience, and has suitable mechanical properties. It is believed that the combination of features described herein strikes a good balance between controlling material costs while providing a superior tactile experience and suitable mechanical properties. It is believed that the features of consolidating bond shapes and patterns described herein may be particularly useful in applications of nonwovens of relatively low basis weights in some applications, in that it is believed that such features provide a way to enhance loft while reducing, or at least without adding, basis weight. Accordingly, for such applications, a nonwoven having a basis weight from about 6.0 gsm to about 50 gsm, from about 10.0 gsm to 45 gsm, from about 15 gsm to about 45 gsm, from about 20 gsm to about 40 gsm, from about 24 gsm to about 40 gsm, greater than about 20 gsm, greater than about 22 gsm, greater than about 24 gsm, greater than about 25 gsm, greater than about 26 gsm, greater than about 28 gsm, greater than about 30 gsm, greater than about 35 gsm, greater than about 40 gsm, greater than about 45 gsm, greater than about 50 gsm, or greater than about 55 gsm, specifically reciting all 0.1 gsm increments within the specified ranges and all ranges formed therein or thereby, may be used. All basis weight measurements are taken in accordance with the Basis Weight Test herein. When used as a component of an absorbent article such as a topsheet, a lower basis weight nonwoven may provide strikethrough superior to that of a higher basis weight nonwoven. A lower basis weight nonwoven may be desirable to a higher basis weight one when used, for example, as a component of a zero-strain stretch laminate, because it may be more accommodating of an activation/incremental stretching process. In other applications, such as, for example, use of nonwovens to form products such as disposable clothing articles, wipes or dusters, higher basis weights up to 100 gsm, or even 150 gsm, may be desired. It is believed that the features of bonding protrusions, bonding shapes and bonding patterns described herein may have beneficial effects on loft and/or softness perception, even with nonwovens of such higher basis weights. Optimal basis weight is dictated by the differing needs in each application, and cost concerns.

A nonwoven web used as a topsheet, or a portion thereof, of an absorbent article of the present disclosure may have a basis weight in the range of about 15 gsm to about 60 gsm, about 20 gsm to about 50 gsm, about 25 gsm to about 50 gsm, about 25 gsm to about 45 gsm, about 25 gsm to about 40 gsm, about 30 gsm to about 38 gsm, greater than about 20 gsm, greater than about 25 gsm, greater than about 30 gsm, greater than about 35 gsm, greater than about 40 gsm, greater than about 45 gsm, or greater than about 50 gsm, specifically reciting all 0.1 gsm increments within the specified ranges and all ranges formed therein or thereby.

It is believed that the desired overall visual softness signals of a backsheet laminate may be better achieved when the backsheet laminate is substantially white in color, and has an Opacity of at least 45%, at least 70%, at least 73%, or at least 75%, as measured by the Opacity Measurement Method set forth below. Accordingly, it may be desirable to add a white-tinting/opacifying agent also to the polymer(s) forming the polymeric film, and to the polymer(s) supplying the spinnerets used to form the fibers of the nonwoven web.

It may be desirable that a white-tinting/opacifying agent be added to the polymer resin that is spun to make the nonwoven. Adjusting the opacity of the nonwoven web, through addition of an opacifying agent, may be desirable, such that the nonwoven web has an Opacity of at least 10%, at least 18%, or at least 40%.

While a variety of whitening/opacifying agents may suffice, it is believed that titanium dioxide ($TiO_2$) may be particularly effective because of its brightness and relatively high refractive index. It is believed that addition of $TiO_2$ to the polymer(s) from which the fibers are to be formed, in an amount up to 5.0% by weight of the nonwoven, may be effective to achieve the desired results. However, because $TiO_2$ is a relatively hard, abrasive material, inclusion of $TiO_2$ in amounts greater than 5.0% by weight may have deleterious effects, including wear and/or clogging of spinnerets; interruption and weakening of the structure of the fibers and/or calender bonds therebetween; undesirably increasing the surface friction properties of the fibers (resulting in a less smooth tactile feel); and unacceptably rapid wear of downstream processing equipment components. It is believed that the increased opacity provided by whitener helps to produce a visually distinctive, soft appearance of the nonwoven. It also may be desired in some applications that a coloring or tinting agent be added to one or more the polymer resin(s) from which the nonwoven fibers will be spun.

Opacity can also be enhanced by using fiber having cross-sectional shapes other than round and solid (non-hollow) geometries, namely trilobal or multilobal cross-sections, or hollow configurations or combinations thereof. Those non-circular cross-sectional shapes can also provide advantages in terms of loft and compression resilience.

Figure 3:
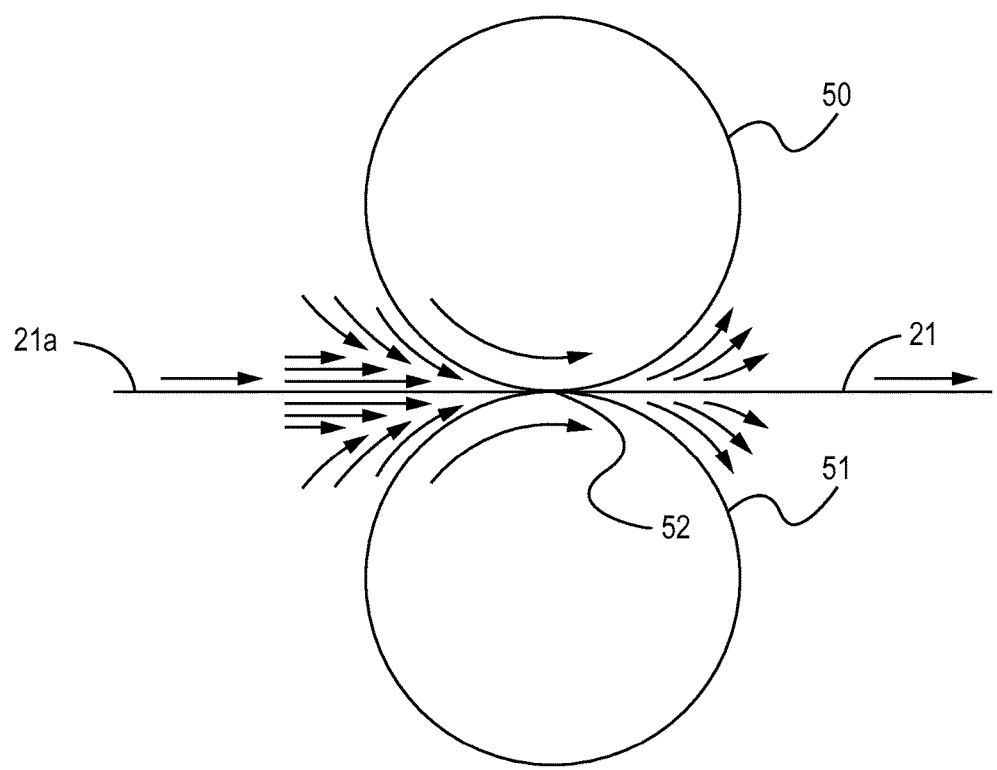
FIG. 3 is a simplified schematic view of a batt moving through the nip between calender rollers to form a calender-bonded nonwoven web.

Spunbonding includes the step of calender-bonding the batt of spunlaid fibers, to consolidate them and bond them together to some extent to create the web as a fabric-like structure and enhance mechanical properties e.g., tensile strength, which may be desirable so the material can sufficiently maintain structural integrity and dimensional stability in subsequent manufacturing processes, and in the final product in use. Referring to FIG. 3, calender-bonding may be accomplished by passing the batt 21a through the nip between a pair of rotating calender rollers 50, 51, thereby compressing and consolidating the fibers to form a nonwoven web 21. One or both of the rollers may be heated, so as to promote heating, plastic deformation, intermeshing and/or thermal bonding/fusion between superimposed fibers compressed at the nip. The rollers may form operable components of a bonding mechanism in which they are urged together by a controllable amount of force, so as to exert the desired compressing force/pressure at the nip. In some processes an ultrasonic energy source may be included in the bonding mechanism so as to transmit ultrasonic vibration to the fibers, again, to generate heat energy within them and enhance bonding.

One or both of the rollers may have their circumferential surfaces machined, etched, engraved or otherwise formed to have thereon a bonding pattern of bonding protrusions and recessed areas, so that bonding pressure exerted on the batt at the nip is concentrated at the bonding surfaces of the bonding protrusions, and is reduced or substantially eliminated at the recessed areas. The bonding surfaces have bonding surface shapes. As a result, an impressed pattern of bonds between fibers forming the web, having bond impressions and bond shapes corresponding to the pattern and bonding surface shapes of the bonding protrusions on the roller, is formed on the nonwoven web. One roller such as roller 51 may have a smooth, unpatterned cylindrical surface so as to constitute an anvil roller, and the other roller 50 may be formed with a pattern as described, to constitute a bonding pattern roller; this combination of rollers may impart a pattern on the web reflecting the pattern on the bonding pattern roller. In some examples both rollers may be formed with patterns, and in particular examples, differing patterns that work in combination to impress a combination pattern on the web such as described in, for example, U.S. Pat. No. 5,370,764.

Figure 4A:
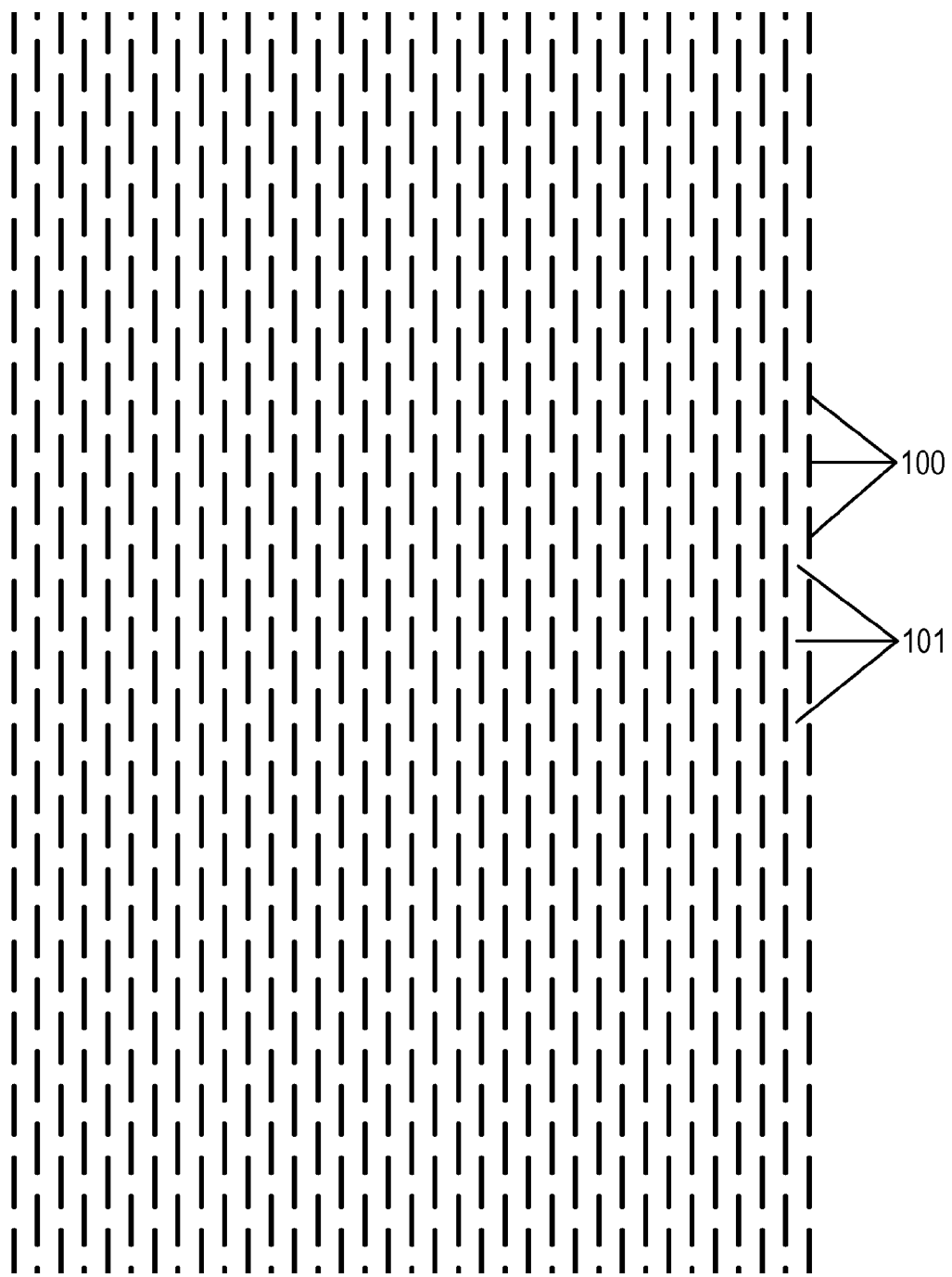
FIG. 4A is a view of a pattern of bonding surface shapes of bonding protrusions that may be imparted to the surface of a calender roller, to create a corresponding pattern of consolidating bond impressions having bond shapes in a nonwoven web.

A repeating pattern of bonding protrusions and recessed areas such as, for example, depicted in FIG. 4A, may be formed onto a bonding roller 50 (FIG. 3). The rod-shaped bonding shapes 100 depicted in FIG. 4A depict raised surfaces of bonding protrusions on a roller, while the areas between them represent recessed areas 101. The bonding shapes 100 of the bonding protrusions impress like-shaped bond impressions on the web in the calendering process.

The bonding protrusions on a roller will have a height, which may be expressed as a difference between the radius of the roller at the outermost (bonding) surfaces of the bonding protrusions, and the radius of the roller at the recessed areas 101. The height may be adjusted with the objective of minimizing the amount of material that must be removed from the roller surface by machining or etching to create the desired shapes and pattern, while still providing for sufficient clearance between the roller bearing the bonding protrusions and the opposing roller, at the recessed areas 101, to accommodate passage of the batt through the nip in areas of the batt not to be bonded (i.e., at the recessed areas), without substantially compressing it—because maximum loft/caliper is the objective. For webs of the type and basis weight contemplated herein, a bonding protrusion height between about 0.3 mm and about 1.0 mm may be desired, or, a bonding protrusion height between about 0.5 mm and about 0.8 mm, or even a bonding protrusion height between about 0.6 mm and about 0.7 mm, specifically reciting all 0.01 mm increments within the specified ranges and all ranges formed therein or thereby. The bonding surfaces of the bonding protrusions may have an average area between about 0.3 $mm^2$ and about 10 $mm^2$, specifically reciting all 0.01 mm increments within the specified ranges and all ranges formed therein or thereby. The bonding protrusions typically have sides with an angled slope when viewed in cross section through the height thereof.

Nonwoven webs of the type contemplated herein may be calender-bonded at line speed greater than 300 m/min., or 600 m/min., or even 800 m/min., or more, depending upon nonwoven web composition, basis weight, bonding pattern, and equipment and process variables selected. Referring again to FIG. 3, it will be appreciated that at such speeds, the batt 21a and the surfaces of rollers 50, 51 may entrain surrounding air and move it toward the nip 52, as suggested by the arrows. Surface features of a bonding roller 50, as described above, may enhance this effect. It is believed that, as entrained air is carried toward the nip, the decreasing space between the rollers as the nip is approached creates a zone of relatively higher, and increasing, air pressure in front of the nip 52. A portion of the entrained air under such higher pressure may be urged into and further compressed in the nip 52, within the recessed areas of the bonding pattern on the roller, and within the interstices of the fibers passing through the nip. It is believed that, as nonwoven web 21 exits the nip 52, compressed air entrained within the fibers and passing through the nip therewith encounters a zone of relatively lower pressure on the exit side, and accelerates away from the nip in all unobstructed directions as a result. Thus, it is believed that substantial air entrainment, air compression and complex air flows of relatively high velocity occur within and about the batt 21a and web 21 as a result of movement of the batt and rotation of the calender rollers in the calender-bonding process.

It is believed that surface features of a bonding roller including the bonding protrusions affect these air flows. Particularly at the nip, the profiles of bonding protrusions present obstructions to airflow, while the recessed areas between the bonding protrusions present passageways. Thus, it is believed that for certain configurations, shapes, and positions of bonding protrusions, as will be reflected in the bond impressions created in the web, rotational orientation(s) and repeating patterns of the bonding shapes can be selected and formed to have a beneficial effect on these air flows. It is believed, further, that patterns of bonding protrusions having bonding surface shapes with certain features, reflected in the bonding surfaces and the cross sections of the protrusions along planes substantially parallel with the bonding surfaces, rotational orientations relative the plane approximated by the web surface, and spacing, may be employed to channel these air flows in a way that causes them to reposition the fibers during the calender bonding process, such as by teasing or fluffing the fibers, thus providing an enhanced calender-bonded nonwoven web having greater loft/caliper than a similar nonwoven web having other consolidated bond shapes and patterns, all other variables being the same.

Figure 5A:
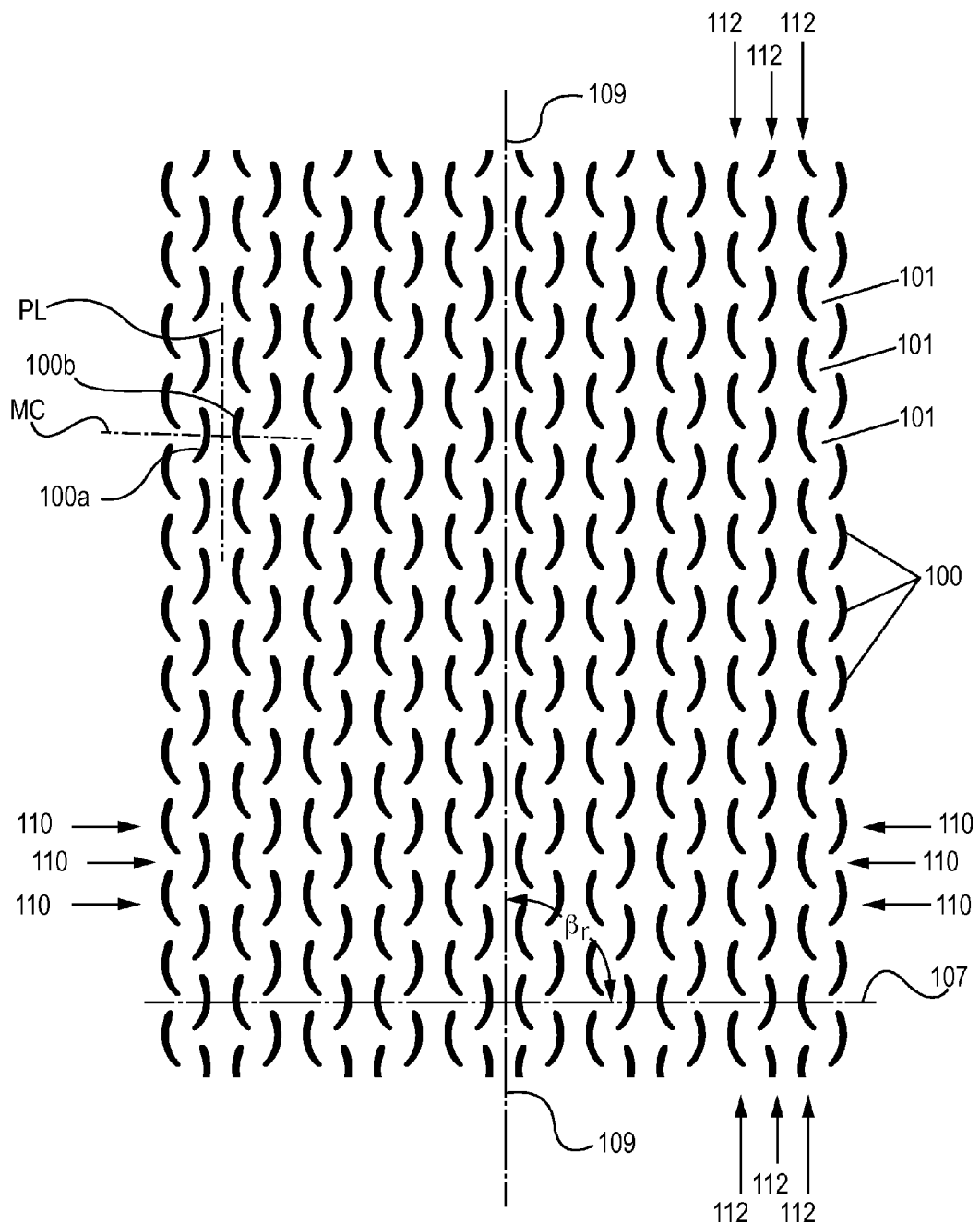
FIG. 5A is a view of another pattern of bonding surface shapes of bonding protrusions that may be imparted to the surface of a calender roller, to create another corresponding pattern of consolidating bond impressions having bond shapes in a nonwoven web.
Figure 5B:
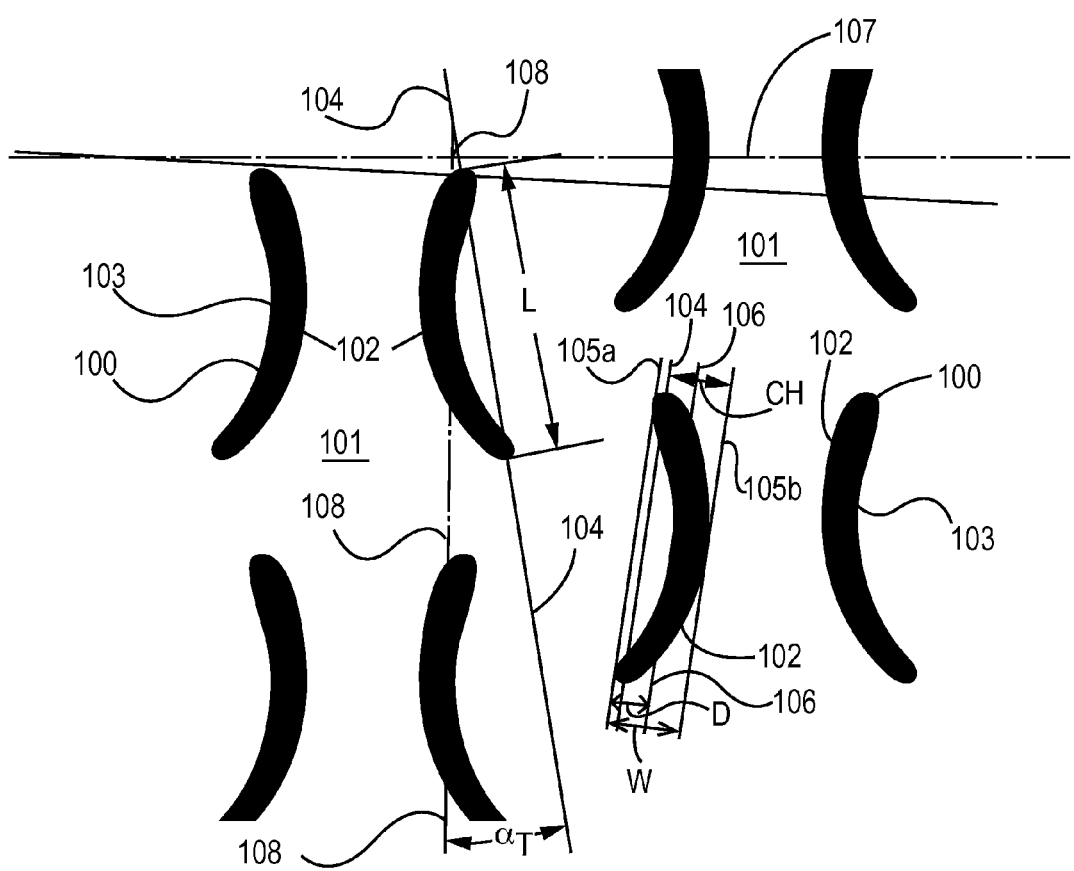
FIG. 5B is a magnified view of the pattern of bonding surface shapes of bonding protrusions or consolidating bond impressions having bond shapes appearing in FIG. 5A.
Figure 5C:
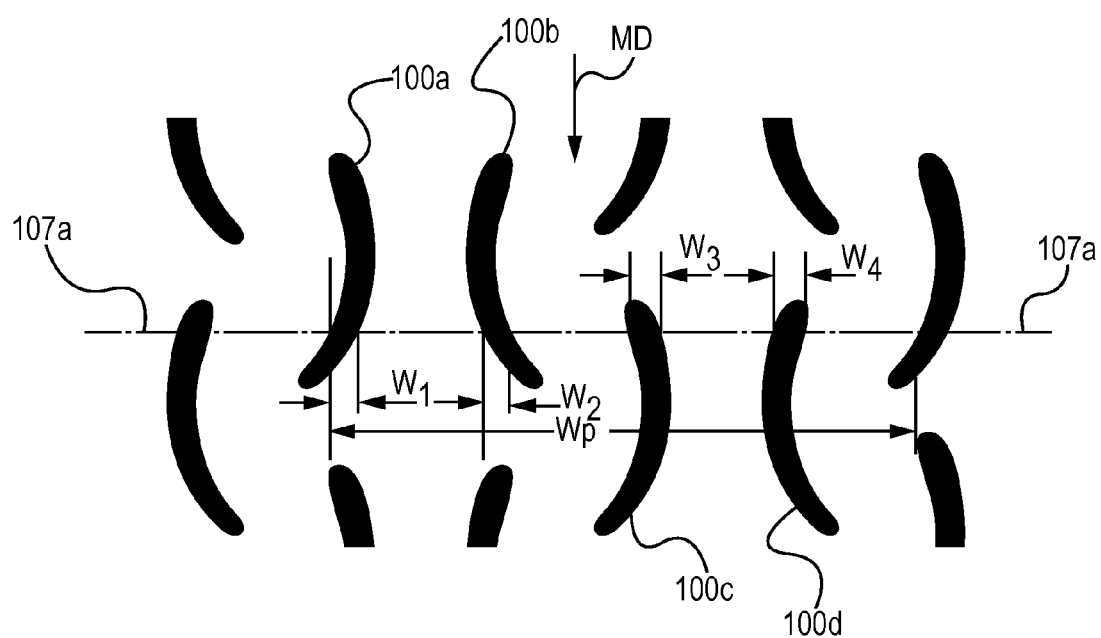
FIG. 5C is a magnified view of the pattern of bonding surface shapes of bonding protrusions or consolidating bond impressions having bonding impressions appearing in FIG. 5A.

FIGS. 5A, 5B and 5C depict one example of a bonding pattern and bonding shapes that may be reflected in bond shapes of bond impressions in a nonwoven web. Bonding shapes 100 represent the shapes of bonding surfaces of bonding protrusions that may be imparted to a bonding roller by etching, machining or other methods. Such bonding protrusions on a bonding roller may impress bond impressions into a web, of like bond shapes, arranged in a like bonding pattern. Without intending to be bound by theory, it is believed that certain aspects and features of the depicted shapes and pattern may have the beneficial effect described above.

Referring to FIG. 5B, the bonding shape 100 has a greatest measurable length L, which is measured by identifying a shape length line 104 intersecting the perimeter of the shape at points of intersection that are the greatest distance apart that may be identified on the perimeter, i.e., the distance between the two farthest-most points on the perimeter. The bonding shape 100 has a greatest measurable width W which is measured by identifying respective shape width lines 105a, 105b which are parallel to shape length line 104 and tangent to the shape perimeter at one or more outermost points that are most distant from shape length line 104 on either side of it, as reflected in FIG. 5b. It will be appreciated that, for some shapes (e.g., a semicircle), one of shape width lines 105a, 105b may be coincident/colinear with shape length line 104. Greatest measurable width W is the distance between shape width lines 105a, 105b. Shapes may have an aspect ratio of greatest measurable length L to greatest measurable width W of at least 2.5, at least 2.7, and at least 2.8. The bond shapes and sizes impressed on the nonwoven web may reflect and correspond with the bonding shapes 100 and sizes thereof on the roller.

Still referring to FIG. 5B, a bonding shape 100 may have a shape perimeter with a convex portion 102, lying on one side of the shape length line 104. FIG. 5B shows also that the convex portion may have a varying radius or radii. The varying radius/radii of the convex portion 102 may render the shape perimeter similar to the profile of the camber of an airfoil in cross section. Viewed another way, the cross-sectional profile of an airfoil has a convex portion and is asymmetric about any line or axis that traverses the profile, which can be identified. The convex portion 102 may have a camber height CH measured as the distance between shape length line 104 and the shape width line 105b that is tangent to the convex portion 102. It is believed that, for maximum beneficial impact on airflow, it may be desirable that the ratio between camber height CH and greatest measurable length L be 0.30 or less, 0.25 or less, but greater than zero. It is believed that a bonding protrusion having a cross section along a plane parallel the bonding surface, fitting this description, repeated and arranged in a pattern, has beneficial effects on acceleration and deceleration of air through nonwoven fibers at and about the nip. Again, the bond shapes and sizes impressed on the nonwoven web may reflect and correspond with the bonding shapes and sizes on the roller.

The shape perimeter may have a convex portion with or without a varying radius on both sides of shape length line 104, such that it has the overall contour of an airfoil with symmetrical camber, in cross section. In another alternative, the shape perimeter may have a convex portion on one side of shape length line 104 and a straight portion on or on the other side of shape length line 104, such that it has the overall contour of an airfoil/aircraft wing with asymmetrical camber, in cross section. In another alternative, the shape perimeter may have a convex portion on one side of shape length line 104 and a concave portion 103 disposed substantially opposite the concave portion, as reflected in FIG. 5B, such that it has the overall contour of an airfoil/aircraft wing with asymmetrical camber and relatively high-loft, low-speed features, in cross section.

The extent of the concavity of concave portion 103 may be quantified by measuring the depth thereof, relative the greatest measurable length. The concavity depth D may be measured by identifying a shape concavity line 106 that is parallel with the shape length line 104 and tangent to the deepest point along the concave portion 103. The concavity depth D is the distance between the shape width line 105a facing the concavity and the shape concavity line 106. The extent of the concavity of concave portion 103 may be expressed as a ratio of concavity depth D to shape length L (hereinafter, "concavity depth ratio"). Although shapes that do not have a concave portion 103 are contemplated, it may be desirable that a bonding shape has a concave portion having a concavity depth ratio between 0.00 and 0.30, between 0.00 and 0.25, and between 0.00 and 0.20. Again, the bond shapes and sizes impressed on the nonwoven web may reflect and correspond with the bonding shapes and sizes on the roller.

Whilst the explanation above refers to bonding protrusions and resulting consolidated bond shapes in the web, which have bonding shape/bond shape perimeters following "convex" and/or "concave" (impliedly, smooth) curves, it may be appreciated that the effect may be substantially realized by approximating such smooth curves with chains of straight line segments. Accordingly, each of the terms "convex" and "concave" herein includes a portion of a shape perimeter formed of a chain of 5 or more straight line segments lying on one side of a shape length line and connected end-to-end, that is each a chord of a smooth convex or concave curve lying on one side of the shape length line, or portion of a curve lying on one side of the shape length line that does not include an inflection point.

Without intending to be bound by theory, it is believed that calender roller bonding protrusions having bonding shapes with one or more features as described above have aerodynamic effects on air flow in and about the nip, that cause acceleration and deceleration of air in and about the interstices of the nonwoven fibers in a way that repositions the fibers, and may effect teasing or fluffing, adding loft and caliper.

Additionally, the rotational orientations of the protrusions affect the orientations of the bonding protrusions at the nip, and it is believed that this has an impact. Bonding shapes 100 and the bonding protrusions supporting them may be arranged along an individual shape tilt angle relative the machine and cross directions. Without intending to be bound by theory, it is believed that the shape tilt angle should not exceed a certain amount for the bonding protrusion to have maximum beneficial effect on air flow. Referring again to FIG. 5B, the shape tilt angle $\alpha_T$ may be expressed as the smaller angle formed by the intersection of an axis along the machine direction 108 and the shape length line 104. It is believed, that the shape and the shape tilt angle have cooperating effects on the air flow. In the case of an asymmetric bonding shape, such as the described airfoil-like shape, it is believed that this asymmetric bonding shape is sufficient for effecting the desired changes in air flow. However, a rotational orientation with a tilt angle of more than zero may enhance the effect. With respect to a bonding shape that is not asymmetric, it is believed that the shape tilt angle $\alpha_T$ provides the desired effects on air flow, such that it then should not be less than 1 degree and should not exceed 40 degrees, 30 degrees, or 20 degrees. It is believed that a shape tilt angle within this range effectively provides air flow through the nip, while at the same time, imparts cross-direction vector components to air flows through the nip. Conversely, a shape tilt angle greater than 40 degrees may create too much of an obstruction to air flow through the nip to have a beneficial effect, and even greater shape tilt angles combined with sufficient density of bonding protrusions may have the effect of creating enough obstruction at the nip to substantially divert airflow from the nip, i.e., toward the sides of the bonding rollers, rather than through the nip. The bond shapes and rotational orientations impressed on the nonwoven web may reflect and correspond with the bonding shapes and rotational orientations on the roller.

It is believed that air flows having cross-direction vector components flowing across or through the batt/web as it passes through and exits the nip may urge fibers in the cross-direction, helping add loft, caliper and/or cross direction tensile strength. It will be appreciated that the fibers of many nonwoven batts are laid down in the nonwoven web manufacturing process with a general machine direction orientation or bias, which tends to result in the finished web having relatively greater machine direction tensile strength, and relatively less cross direction tensile strength. Thus, any process that tends to impart some added cross-direction orientation to the fibers prior to bonding may be useful for increasing cross direction tensile strength, bringing about better balance between machine direction tensile strength and cross-direction tensile strength, and adding loft such as by repositioning of the fibers in the z-direction. It is believed that, for best results, it may be even more desirable that shape tilt angle $\alpha_T$ is between about 5 degrees and about 15 degrees, between about 8 degrees and about 12 degrees, and between about 9 degrees and about 11 degrees, specifically reciting all 0.1 degree increments within the specified ranges and all ranges formed therein or thereby, for the most beneficial effects on airflow at the line speeds contemplated herein. The rotational orientation of the bonding pattern impressed on the nonwoven web may reflect and correspond with the rotational orientation of the bonding pattern on the roller.

As suggested above, in order to gain the benefit of energy from a substantial mass of air flowing through the nip, it is also believed desirable that a pattern of bonding protrusions not be excessively obstructive of air flow through the nip, nor that it remove too much energy from the air flow by overly slowing, or halting, and absorbing the energy from, forward (machine-direction) momentum of air flows. Referring to FIG. 5C, a nip line 107a along the cross direction is identified along a pattern where the bonding shapes occupy the greatest proportion of distance along a cross direction line that can be identified in a pattern. Thus, nip line 107a located as shown represents a cross-direction line along which bonding protrusions presented the greatest amount of obstruction that can be identified in a particular pattern, to air flow through the nip, during the bonding process. A repeating series of shapes can be identified; in this example, the repeating series consists of the four shapes 100a, 100b, 100c and 100d. Widths $w_1$, $w_2$, $w_3$, and $w_4$ of the identified shapes 100a, 100b, 100c, 100d in the repeating series reflect restriction of air flow along the nip line 107a. Width $w_p$ is the width of the entire repeating series, including the distances between the bonding shapes. The proportion of maximum restriction along the nip length for the pattern is reflected by the ratio $(w_1+w_2+w_3+w_4 \ldots +w_n)/w_p$, referred to herein as the nip airflow restriction ratio (where "w" is the cross-direction width along the nip line 107a of a bonding shape perimeter, and "n" is the number of bonding shapes along nip line 107a that make up a repeating series). In order that a bonding pattern allows for effective air flow through the nip in order to take advantage of energy of moving air, it may be desirable that the nip airflow restriction ratio be 0.40 or less, 0.30 or less, and 0.25 or less. The bond shapes, rotational orientations and density/numerosity per unit surface area of bond impressions on the nonwoven web may reflect and correspond with the bonding shapes, rotational orientations and density/numerosity per unit surface area of bonding protrusions on the roller, and thus, also reflect the airflow restriction ratio.

Figure 6A:
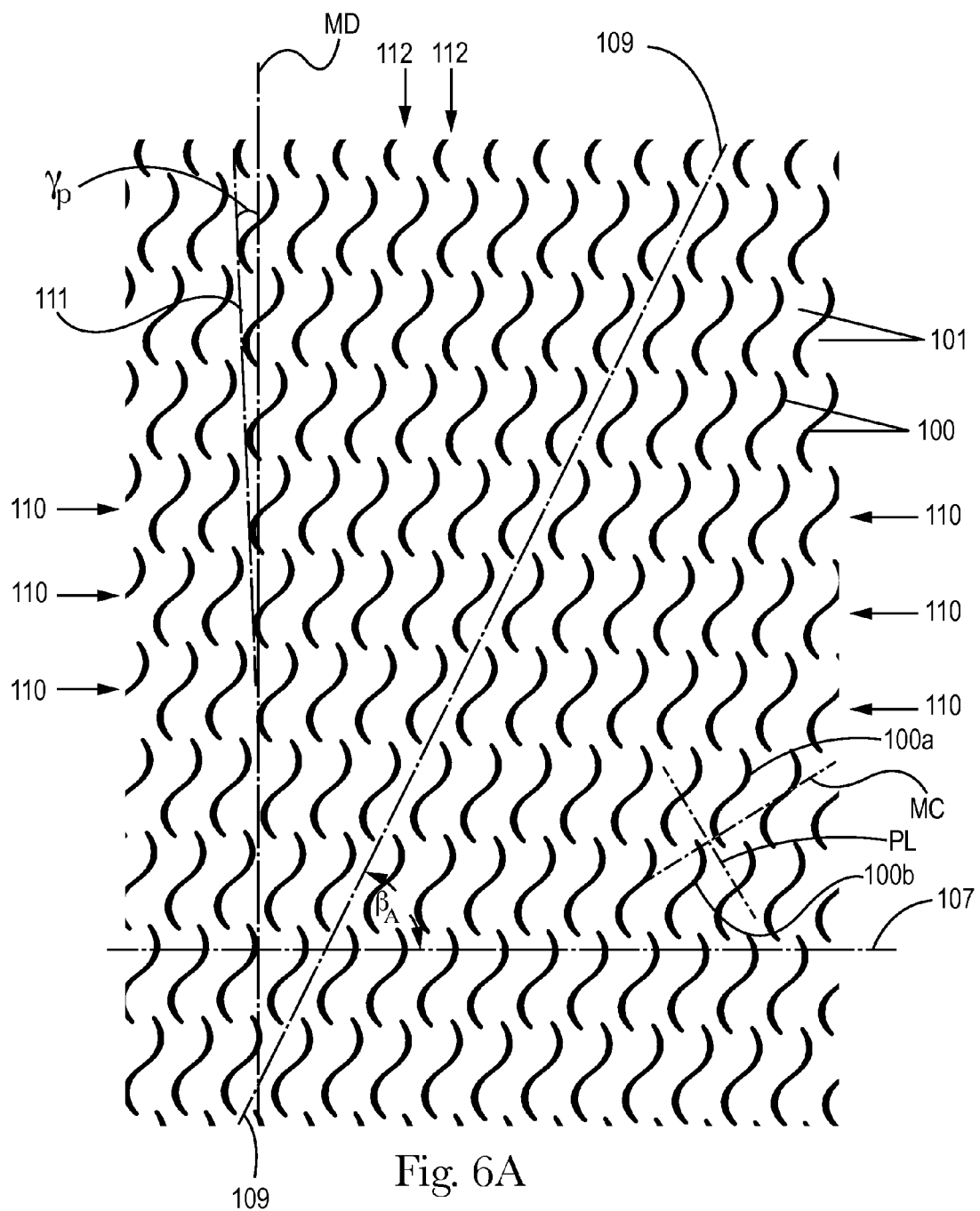
FIG. 6A is a view of another pattern of bonding surface shapes of bonding protrusions that may be imparted to the surface of a calender roller, to create another corresponding pattern of consolidating bond impressions having bond shapes in a nonwoven web.
Figure 6B:
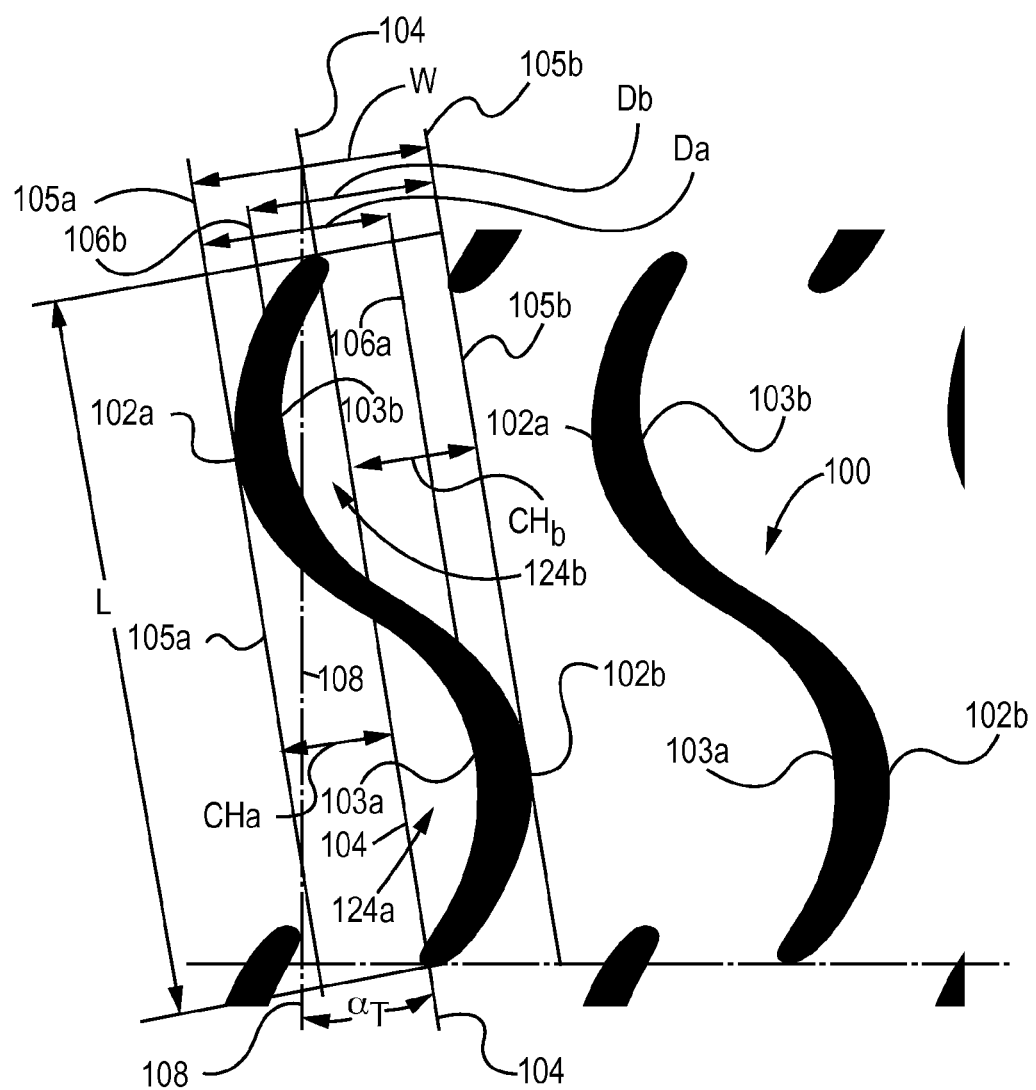
FIG. 6B is a magnified view of the pattern of bonding surface shapes of bonding protrusions or consolidating bond impressions having bond shapes appearing in FIG. 6A.

Referring to FIGS. 6A and 6B, an alternative bonding pattern is depicted. The repeated bonding shape 100 and profile of the associated bonding protrusion is a composite of two generally convex/concave sub-shapes joined or superimposed at their respective tips, in reversed orientation, to form an open "S" shape which is rotationally symmetric about this juncture of the component sub-shapes, respectively its middle inflection point. It will be appreciated, however, that the depicted repeated "S" shape may have several of the features of the bonding shape depicted in FIGS. 5A and 5B, described above, which are believed to be beneficial. The depicted bonding shape 100 in FIGS. 6A and 6B has a greatest measurable length L and greatest measurable width W, measured with respect to shape length line 104 and shape width lines 105a, 105b, identified in the manner described above. As set forth above, bonding shapes 100 within the scope of the present disclosure have an aspect ratio of greatest measurable length L to greatest measurable width W of at least 2.5, at least 2.7, or at least 2.8.

The depicted bonding shape in FIGS. 6A and 6B also has convex portions 102a, 102b along its perimeter. One or both of the convex portions 102a, 102b may have varying radii, and have camber heights $CH_A$ and $CH_B$. It is believed that, for maximum beneficial impact on airflow, it may be desirable that the ratio between camber height CH and the greatest measurable length L also be 0.30 or less, 0.25 or less, but greater than zero.

The depicted bonding shape also has concave portions 103a and 103b along its perimeter. Concavity depth Da is the distance between shape width line 105a facing concavity 103a, and shape concavity line 106a. Concavity depth Db is the distance between shape width line 105b facing concavity 103b, and shape concavity line 106b. Although bonding shapes that do not have a concave portion 103a, 103b along their perimeters are contemplated, it may be desirable that a bonding shape perimeter has one or more concave portions such as concave portions 103a, 103b having a concavity depth ratio:

Concavity depth/$(L*nc)$≤0.30, 0.25, or 0.20, where nc is the number of fully enclosed shapes that are defined by portions of the bonding shape perimeter and the shape length line, which evidence concavities. For example, for the "S" shape shown in FIG. 6B, nc=2 because there are 2 such fully enclosed shapes 124a and 124b.

The shapes 100 in FIGS. 6A and 6B also may have a shape tilt angle $\alpha_T$ determined as set forth above, and within the ranges set forth. The geometric features of the bond shapes and pattern on the nonwoven web may reflect and correspond with those of the shape, size, rotational orientation, density and arrangement of the bond shapes 100.

It is also believed that arranging the bonding protrusions in a pattern such that a relatively straight, unobstructed passageway between them exists along recessed areas 101 at the nip, at least partially along the machine direction, may have beneficial effects. Referring to FIGS. 5A and 6A, it can be seen that each example has a cross-nip airflow line 109 that can be identified, that intersects no bonding shape, and intersects a cross direction axis 107 at an angle such that it has a machine direction vector component. Cross-nip airflow line 109 intersects cross direction axis 107 to form a smaller angle, identified herein as cross-nip airflow angle $\beta_A$. It is believed that cross-nip airflow angle $\beta_A$ may be greater than 45 degrees, between 50 degrees and 90 degrees, or between 60 degrees and 90 degrees, specifically reciting all 0.1 degree increments within the specified ranges and all ranges formed therein or thereby. It is believed desirable that cross-nip airflow line 109 should extend indefinitely without intersecting a bonding shape 100, but at a minimum, past at least 8 rows 110 of bonding shapes 100 without intersecting a bond shape. Again, geometric features of the bond shapes and pattern on the nonwoven web may reflect and correspond with those of the shape, size, rotational orientation, density and arrangement of the bond shapes 100.

Another aspect of the bonding shapes and patterns depicted in, e.g., FIGS. 5A-6B is that they may have any combination of the above-described aspect ratios, maximum nip airflow restriction ratio (0.40 or less), shape asymmetry, shape tilt angles, and other features, and may also reflect use of adjacent pairs of bonding protrusions that define air passageways through the nip that alternately narrow and widen, or converge and diverge, in the manner of a venturi. For example, referring again to FIGS. 5A and 6A, two adjacent bond shapes 100a, 100b may be identified. Herein, "adjacent" means that at least portions of the perimeters of a pair of shapes face each other with no intervening shapes between them; and that the pair of shapes has machine-direction overlap. The pair of shapes has machine-direction overlap if one or more cross-direction lines 107 that are tangent to and/or cross the perimeters of each of the shapes may be identified. A minimum passageway clearance line MC may be identified connecting the perimeters of the shapes 100a, 100b, at the location where the shortest measurable distance between the perimeters exists. The minimum passageway clearance line MC may necessarily meet the perimeter of each of the adjacent shapes where line MC is normal to the perimeter, and line MC identifies the point of greatest constriction of an air passageway between the shapes (i.e., through the corresponding bonding protrusions) proximate and through the nip. A passageway line PL may be identified, perpendicular to the minimum passageway clearance line MC and lying between the adjacent shapes 100a, 100b.

The minimum passageway clearance line MC crosses and identifies a "venturi passageway" if the perimeter of each of the adjacent shapes 100a, 100b diverges away from the passageway line PL moving along the perimeter away from the minimum clearance line MC in both directions. It can be seen in FIGS. 5A and 6A that adjacent shapes 100a, 100b embody this feature.

Without intending to be bound by theory, it is believed that such venturi passageways have the effect of causing localized zones of acceleration and deceleration, and increases and decreases in pressure, as well as turbulence, of air as it passes through the nip. It is believed that these effects serve to tease and/or fluff the fibers of the batt and web about the nip.

For purposes of downstream handling and manufacturing processes, it may be desirable to ensure that no line along the machine direction exists along the nonwoven web surface that is indefinitely long without intersecting a bond impression. This condition (indefinitely long machine direction strip of web without bonds) may result in relatively long lengths of unbonded fibers that may be prone to moving away from a cutting knife in downstream machine direction web slitting operations, resulting in a poorly defined or sloppy slit edge. Additionally, such long, unbonded fibers may also separate from a manufactured edge or slit edge of the web (fraying), which may cause other difficulties in downstream operations. To avoid this condition, it may be desirable to impart a pattern angle $\gamma_P$ to the bonding pattern. Referring to FIG. 6A, pattern angle $\gamma_P$ may be expressed as the smaller angle formed by the intersection of a line 111 connecting like points on repeating, similarly oriented shapes in columns 112, and a machine direction axis. To avoid the above-mentioned problems, it may be desirable that pattern angle $\gamma_P$ be greater than 0 degrees. A pattern angle greater than 0 degrees may ensure that an indefinitely long machine direction strip of web without bonds may not exist. To avoid creating complications with respect to the air flow benefits of the pattern, however, it may be desirable to limit pattern angle $\gamma_P$ to 4 degrees or less, 3 degrees or less, or 2.5 degrees or less. Again, features of the bond pattern on the nonwoven web including pattern angle may reflect and correspond with those of the pattern and pattern angle $\gamma_P$ on the roller.

The features described above apply to the shapes of bonding surfaces of bonding protrusions in a pattern on a bonding roller, and it will be understood that these features are impressed by the roller into the nonwoven batt to form bond impressions having bond shapes and bonds thereat, to form the calender-bonded nonwoven web. As impressed into a nonwoven web, the bonding shapes are reflected as bond shapes, and are identifiable, and measurable in the web, in laminates that include such nonwoven web as a composite layer, and in composite products made from such nonwoven web and/or such laminates.

An additional aspect that it believed important is bonding area of a roller, reflected in bond area on the web. Imagining a pattern of bonding surfaces having shapes reflected in FIGS. 5A and 6A impressed on a surface of a nonwoven web, bonding area and bond area is the area occupied by the bonding shapes on the roller and bond shapes impressed on the surface of the web. In the field of nonwoven web manufacturing, bonding area is often expressed as a percentage, calculated as:

$$\text{Bonding Area \%} = \left[ \frac{\begin{pmatrix} \text{bonding area within} \\ \text{a surface area unit} \end{pmatrix}}{\begin{pmatrix} \text{total surface area of} \\ \text{the surface area unit} \end{pmatrix}} \right] \times 100\%$$

The bonding area reflects the combination of bonding protrusion density (number of bonding protrusions per unit surface area) and average surface area of the bonding shapes 100 in the unit surface area. Thus, increasing the number of bonding protrusions and/or increasing the surface area of the individual bond shapes 100 increases the bonding area, and vice versa. It is believed that bonding area has an impact on the entrainment of air as well as the proportion of entrained air carried toward the nip, which may pass through the nip. If bonding area is relatively greater, this means that more and/or larger bonding protrusions are present at the nip point at any time to obstruct air flow through the nip; conversely, if bonding area is relatively less, this means that fewer and/or smaller bonding protrusions are present at the nip point at any time to obstruct air flow through the nip. Bond area has another effect as well. Increasing bond area increases the number and proportion of the fibers in the nonwoven web that are bonded together, and vice versa. Within a certain range of bond area, tensile strength of the nonwoven web in the machine and/or cross directions may be increased by increasing the bond area. However, bending stiffness of the nonwoven web may be correspondingly increased, and loft decreased—compromising the soft feel and/or appearance of the nonwoven. In order to best realize the benefits of air flow, air compression and channeling believed to be occurring through use of the bond shapes described herein, enhancing loft, while still imparting satisfactory tensile properties to the web, it is believed that bonding area should be in the range of about 4.0% and about 18%, between about 6% and about 16%, or between about 8% and about 14%, specifically reciting all 0.1 degree increments with the specified ranges and all ranges formed therein or thereby. At the line speeds contemplated herein, and relative to the bonding area, the average surface area per bonding shape affects bonding area and bonding protrusion density. It is believed desirable that the average bonding shape 100 surface area be in the range of 0.3 mm$^2$ and 10 mm$^2$. Correspondingly, it is believed desirable that the density of the bonding protrusions, and correspondingly, the impressed bond shapes, be between 0.4 bonding protrusions/cm$^2$ for bonding shape/bond shape area of 10 mm$^2$ at 4% bonding area and 60 bonding protrusions/cm$^2$ for bonding shape/bond shape area of 0.3 mm$^2$ at 18% bonding area Similar calculations of bonding protrusion density and average bond shape surface area to arrive at the bond areas in the ranges set forth above, will be appreciated. The surface area and density of bond shapes impressed on the nonwoven web may reflect and correspond with those of the bonding shapes, and thus, the bond area on the web may reflect and correspond with the bonding area on the roller as well.

It is also believed that the speed of travel of the batt toward the bonding nip (batt line speed) is important. It will be appreciated that, if the batt line speed is too slow, air mass entrained by the batt as it approaches the nip may not have sufficient linear momentum to maintain a large enough zone of sufficiently elevated air pressure at the entry side effective to ensure that substantial air mass is urged through the nip, rather than being merely urged around the nip and the rollers along alternate pathways. Accordingly, it is believed that line speed at which the batt is conveyed toward the nip should be equal to or greater than 300 meters/minute, equal to or greater than 600 meters/minute, or equal to or greater than 800 meters/minute.

It is believed that use of a calender roller having bonding patterns and bonding shapes as described herein take advantage of air flows resulting from entrainment of air along a moving nonwoven batt and calender rollers, and air compression, that occur during calender-bonding, in a way that causes the resulting nonwoven web to have enhanced loft and a soft feel. It is believed also that the bonding shapes need not be all of like kind or rotational orientation, but rather, that suitable combinations of differing shapes including bonding shapes having features as described herein, and optionally, in combination with other shapes, may be used and included. Employment of the described features may reduce or eliminate a need for other loft enhancement processes, such as hydroengorgement or hydroentanglement—which may save costs of additional equipment and operation.

In addition to the above-described features and processes that may be useful for producing a nonwoven web with relatively enhanced loft, other features and processes may be employed. Processes such as carding, hydroengorgement, hydroentanglement and bi-component spunbond production may be effective for producing relatively low-density nonwoven web materials. Hydroentanglement and/or hydroengorgement are described in, for example, U.S. Pat. Nos. 6,632,385, 6,803,103, and 7,858,544, and U.S. Pat. App. Pub. No. 2012/0094567. Hydroengorgement in combination with other processes and features is disclosed in, e.g., U.S. application Ser. No. 13/213,177. Features and processes for production of bi-component, crimped fibers with enhanced loft are described in, for example, U.S. Pat. No. 7,789,870; U.S. Pat. Pub. No. 2007/0275622; European Pat. App. No. EP 1 369 518 A1; and PCT App. No. WO 2007/097467.

In addition to relatively low density (i.e., high loft) attributes for a nonwoven, it is believed from consumer research that relatively low surface friction (i.e., a relatively smooth, gliding or slippery feel) can enhance tactile perceptions of softness. Any of several combinations of materials and processes may be employed to produce a nonwoven having a relatively slippery feel, i.e., relatively low coefficients of friction along its surface. One approach includes forming the nonwoven from fibers composed partially or entirely of polyethylene. Relative to other materials deemed useful and economically practically for the manufacture of nonwovens of the types contemplated herein (such as, for example, polypropylene), polyethylene provides a relatively slippery feel (relatively low coefficients of friction). For example, a bicomponent fiber having a polyethylene component in a side-by-side arrangement (polyethylene forms portions of outer surfaces of fibers), or even in a core-sheath arrangement (polyethylene forms substantially all of outer surfaces of fibers, may be deemed suitable. Another approach may involve coating the nonwoven surfaces or fibers thereof with a silicon-based topical coating, to impart a slippery feel.

As noted, some types of disposable absorbent articles such as diapers may have absorbent cores that contain particles of absorbent polymer material, which serves to absorb and store liquid exudates. In some designs, the absorbent cores also include cellulosic fiber material (airfelt), also included to help absorb and store liquid exudates, but also included to provide a matrix in which absorbent polymer particles are dispersed and distributed, so as to prevent gel blocking. Other core designs, however, do not rely upon, and may have portions that do not include, cellulosic fiber material. For example, some core designs may reply upon adhesive to retain the absorbent polymer particles in dispersed and distributed locations along the core, and thus, such cores may have substantial portions along their lengths in which relatively little or no airfelt is included.

Disposable absorbent articles such as diapers having cores with absorbent polymer particles but a relatively low amount of cellulose fibers, or diapers with absorbent cores that are substantially airfelt-free along portions of their lengths, may in some circumstances be less likely to be perceived as relatively "soft," all other factors being equal. Absorbent cores of designs that include substantial quantities of cellulosic fiber for fluid absorption and/or storage tend to be bulkier and thicker, and the cellulose fiber batt or wad tends to be relatively highly compressible in the hands. These attributes may combine to promote perceptions of softness.

Conversely, absorbent cores of designs that rely substantially only on particulate absorbent polymer materials for fluid absorption and/or storage, with comparatively low or substantially eliminated quantities of cellulosic fibers along some or all of their lengths, tend to be thinner and relatively less compressible in the hands. These attributes may combine to reduce perceptions of softness. It is believed, also, that in absorbent cores having particulate absorbent polymer materials and relatively low quantities of cellulosic fibers along some or all of their lengths, the relatively hard individual particles, or relatively hard deposits of particles, may be felt by the hands through the enveloping layers of the article containing the particles, thus imparting a tactile granular feel that is believed to negatively impact softness perceptions. The granular feel results from concentrations of pressure perceivable upon squeezing or similar manipulation, localized over the individual particles or deposits. In other words, the individual particles or deposits create tactile "pressure points."

Similarly, the presence of elastic members such as elastic strands between nonwoven web materials respectively forming the outermost and innermost layers of the diaper (including but not limited to the topsheet and backsheet), included to form, e.g., leg cuffs (longitudinally-oriented strands), elasticized waistbands (laterally-oriented strands), or elasticized side panels (laterally-oriented strands), may create tactile pressure points or ridges giving a ribbed or ridged feel to the diaper.

Through research it has been learned that some consumers, when asked to evaluate the softness of samples of disposable diapers provided to them, naturally tend to conduct their evaluations in part by gripping the diapers between the thumb and one or more of the fingers, for example, with the thumb over and contacting the topsheet 18 and the finger(s) beneath and contacting the backsheet 20 (with reference to FIG. 2A) and squeezing them and rubbing them between thumb and finger(s). For diapers having absorbent cores having particulate absorbent polymer materials and relatively low quantities of cellulosic fibers, and for diapers having elastic strands sandwiched between outermost and innermost layers, this manner of evaluation may result in the consumer quickly noticing the pressure points.

It has been discovered, however, that selection of component materials for topsheet and backsheet having particular attributes in combination may impact the manner in which the softness of the diaper structure is perceived. It has been found that selection of particular combinations of attributes can reduce or mask the pressure points, or make them less likely to be noticed by consumers.

As noted, the topsheet and the outermost layer of the backsheet may be respectively formed of nonwoven web materials. These nonwoven web materials may comprise a three-dimensional texture in at least portions thereof. The three-dimensional texture may be formed by embossing, aperture/embossing, hydroengtangling, or other suitable three-dimensional material forming techniques. The three-dimensional material may comprise projections, recesses, and/or apertures. Apertures may be formed at the bottom of the recesses or at the top of the projections.

It is believed that these nonwoven web materials may be imparted with a minimum basis weight, and a minimum loft or caliper per unit basis weight, or, expressed differently, a maximum density, to effectively promote or maintain satisfactory impressions of softness. In another particular, these materials may be imparted with a minimum compression loft (as determined by the Compression Loft measurement method set forth below), which reflects the relative loftiness of the material and, independent of its density. If each of these nonwoven web materials satisfy such criteria, they may be sufficiently effective to diffuse pressure away from pressure points over particles of absorbent polymer, or otherwise make the pressure points less noticeable, when the diaper is handled.

For these reasons, it may be desired that the nonwoven web materials forming the topsheet and the outer layer of the backsheet have a combined basis weight of at least about 25 gsm, at least about 30 gsm, at least about 35 gsm, at least about 40 gsm, at least about 45 gsm, at least about 50 gsm, at least about 55 gsm, at least about 60 gsm, at least about 65 gsm, at least about 70 gsm, at least about 75 gsm, at least about 80 gsm, or may be in the range of about 25 gsm to about 80 gsm, about 30 gsm to about 70 gsm, about 35 gsm to about 60 gsm, about 35 gsm to about 55 gsm, about 35 gsm to about 55 gsm, about 35 gsm to about 50 gsm, or about 40 gsm to about 50 gsm, specifically reciting all 0.1 gsm increments within the specified ranges and all ranges formed therein or thereby. In combination, it may be desired that each of the nonwoven web materials have a pre-conversion density no greater than 65 kg/m$^3$, or no greater than 55 kg/m$^3$, where "pre-conversion density" for a particular nonwoven web material is determined at the point in the manufacturing process at which the material is first unwound from its supply roll after having been manufactured, gathered and stored on the roll. Also, in combination with the above-specified density and basis weight, or in another combination with basis weight, it may be desired that each of the nonwoven web materials has a compression loft of at least 30%, at last 40%, at least 50%, at least 60%, or at least 70%.

It will be appreciated that loft can be increased, and thus density decreased, by use of any of the materials, and by any of the various processes and techniques effective for imparting, preserving or enhancing loft of a nonwoven described herein, or described in prior art references cited and incorporated by reference herein.

While increasing basis weights of these respective nonwoven web materials (which may generally tend to increase caliper, all other factors being equal) may be effective to diffuse pressure away from tactile pressure points, and it may be intuitive that increasing basis weight without constraint may be particularly effective, the manufacturer is always under cost constraints. Since increasing basis weight of any particular component web material may add material cost, increasing basis weight to a degree deemed most satisfactory for diffusing pressure away from pressure points may be unacceptably costly.

It is believed, however, that another cost-mitigating strategy may be effective. It is believed that if one of the nonwoven web materials forming the topsheet and outer layer of the backsheet is significantly different from the other with respect to certain attributes, this can have a negative impact on softness perceptions. It is believed that certain attributes of a nonwoven are pressure-diffusing attributes, meaning that they may serve to diffuse the pressure and resulting tactile sensation created by a pressure point over a particular of absorbent polymer material. It is believed that attributes such as but not necessarily limited to compression loft, density, basis weight, and frictional properties (i.e., the tactile "slipperiness" of the material) are pressure-diffusing attributes. Without intending to be bound by theory, it is believed that a substantial imbalance between pressure diffusing attributes of the respective nonwoven web materials forming the topsheet and outer layer of the backsheet may have the effect of causing the observer to be more likely to notice pressure points on the side of the article (i.e., the wearer-facing topsheet side or the outward-facing backsheet side) formed of the nonwoven web material with the lesser of the pressure-diffusing attributes. It is believed that such an imbalance has an exacerbating effect particularly when, for example, the respective nonwovens are of relatively low basis weights.

Conversely, if these materials are selected so as to be sufficiently similar or relatively balanced with respect to certain pressure diffusing attributes, this can have a positive impact on softness perceptions. It is believed, further, that such balance can have a synergistic effect when combined with pressure diffusing attributes, such that a combination of such balance with pressure diffusing attributes of the nonwoven web materials can allow use of nonwoven materials of relatively lower basis weights than might otherwise be expected, while still being sufficient to effectively mask tactile pressure points or make them less noticeable to the consumer.

Thus, it may be desired that, in combination with the combined basis weight of the respective nonwoven web materials forming the topsheet and the outer layer of the backsheet, the ratio of one or any combination of the basis weight, density and compression loft, of the nonwoven web material forming the topsheet and the nonwoven web material forming the outer layer of the backsheet may be from 10/90 to 90/10, from 20/80 to 80/20, from 25/75 to 75/25, from 30/70 to 70/30, from 35/65 to 65/35, from 40/60 to 60/40, from 45/55 to 55/45, or even 50/50, specifically reciting all ratios within the specified ranges and all ranges formed therein or thereby. It may also be desired that the respective materials have respective coefficients of static and kinetic friction no greater than certain amounts. Additionally, it may be desired that the respective coefficients of friction of the respective nonwoven web materials are within 70, 65, 60, 55, 50, 45, 40, 35, 30, 25, 20, or, 15, 10, or 5 percent of each other (where the percent differential is the ratio of the difference between the respective coefficients divided by the smaller of the two, multiplied by 100%).

Imparting one or more of such balances of attributes in selection of these respective materials may enable usage of nonwoven web materials having combined basis weights (for nonwoven web materials forming topsheet and outer layer of backsheet) no more than about 80 gsm, no more than about 75 gsm, no more than about 70 gsm, no more than about 65 gsm, no more than about 60 gsm, no more than about 55 gsm, no more than about 50 gsm, no more than about 45 gsm, no more than about 40 gsm, or no more than about 35 gsm, providing for effective masking and/or reduced perception of tactile pressure points while enabling observation of cost constraints on basis weight.

Examples of Nonwoven Web Materials for Topsheet and Backsheet Outer Layer

In following examples for the manufacture of nonwoven webs, if it is not defined differently, the batt was produced from 3 following spunbond beams on REICOFIL 4 technology, using the four different bonding patterns indicated:

Pattern "Wing-shape" (as depicted in FIG. 5)
    Bonding area percentage=12.4%
    Bonding protrusions/cm$^2$=3.1
    Angle $\alpha_T$=10°
    Angle $\beta_A$=90°
    Angle $\gamma_P$=1°
    L=6.2 mm
    W=1.7 mm
    D=0.9 mm
    CH=1.4 mm
    Distance between beginning of repeating shapes in columns=8 mm
    Distance between beginning of repeating shapes in rows=8 mm
    Bonding protrusion height=0.65 mm Pattern "S-shape" (as depicted in FIG. 6)
    Bonding area percentage=12.9%
    Bonding protrusions/cm$^2$=1.5
    Angle $\alpha_T$=10°
    Angle $\beta_A$=60°
    Angle $\gamma_P$=1°
    L=12.2 mm
    W=4.0 mm
    $D_A$=3.1 mm
    $D_B$=3.1 mm
    $CH_A$=1.9 mm
    $CH_B$=2.1 mm
    Distance between beginning of repeating shapes in columns=11.4 mm
    Distance between beginning of repeating shapes in rows=6.0 mm
    Bonding protrusion height=0.65 mm Pattern "S-shape v2" according to the present disclosure (FIG. 7)
    Bonding area percentage=13%
    Bonding protrusions/cm$^2$=2.4
    Angle $\alpha_T$=10°
    Angle $\beta_A$=63°
    Angle $\gamma_P$=1°
    L=9.2 mm
    W=3.0 mm
    $D_A$=2.3 mm
    $D_B$=2.3 mm
    $CH_A$=1.3 mm
    $CH_B$=1.6 mm Distance between beginning of repeating shapes in columns (DRC)=8.8 mm
Distance between beginning of repeating shapes in rows (DRR)=4.65 mm
Bonding protrusion height=0.75 mm Comparative pattern "Standard bulky" described in patent application WO 2009/021473 (depicted in FIG. 4A).
Bonding area percentage=14.0%
Bonding protrusions/cm$^2$=9
Angle $\alpha_T$=0°
Angle $\beta_{A1}$=90°
Angle $\beta_{A2}$=55°
Angle $\gamma_P$=0°
L=3.4 mm
W=0.4 mm
D=0 mm
CH=0.2 mm
Distance between beginning of repeating shapes in columns=5.6 mm
Distance between beginning of repeating shapes in rows=2.0 mm
Bonding protrusion height=0.7 mm Comparative pattern "Standard"—(oval shape, depicted FIGS. 4B, 4C)
Bonding area percentage=18.1%
Bonding protrusions/cm$^2$=49.9
Angle $\alpha_T$=60°
Angle $\beta_A$—does not exist
Angle $\gamma_P$=0°
L=0.9 mm
W=0.5 mm
D—does not exist
CH=0.3 mm
Distance between beginning of repeating shapes in columns=1.5 mm
Distance between beginning of repeating shapes in rows=2.6 mm
Bonding protrusion height=0.6 mm Relative Humidity While wishing not to be bound by any particular theory, it is believed that softer materials are desirable on topsheets and/or outer cover nonwoven materials of backsheets to reduce skin irritation and provide comfort to the wearer. These softer materials, however, typically may require an increase in the basis weight of these materials to achieve such softness benefits. The issue with the higher basis weight materials, especially when used as a topsheet, or portion thereof, is that they may retain more moisture at or near the skin than lower basis weight materials. A majority of this moisture may be wicked through the high basis weight materials of the topsheets, through an acquisition/distribution system comprising one or more layers, into a conventional absorbent core comprising a high amount of cellulosic fibers (e.g. 30% or more), by weight of the absorbent core, mixed with AGM. The high concentrations of cellulosic fibers in the conventional cores may not fully "lock away" moisture after, for example, one or more urination events, like AGM "locks away" moisture. The cellulosic fibers instead allow the moisture to evaporate back up toward the topsheet. This evaporation leads to more moisture and water vapor partial pressure within the absorbent article and, thereby, more moisture in contact with the wearer's skin. To reduce moisture in contact with the wearer's skin, the present disclosure provides a substantially cellulose free absorbent core, or a cellulose free absorbent core. The absorbent core with no or very limited cellulosic fibers, or a vast majority of, AGM, better "locks away" moisture within the absorbent core and at least inhibits the moisture and water vapor partial pressure from rising back toward the topsheet and contacting the wearer's skin. This allows the absorbent article to provide a lower relative humidity environment in the absorbent article for the wearer leading to reduced skin irritation, even when paired with a high basis weight topsheet.

The relative humidity in a diaper with a substantially cellulose free absorbent core, or cellulose free absorbent core, and a high basis weight topsheet and, optionally, a high basis weight outer cover nonwoven of a backsheet may have a relative humidity in the range of about 30% to about 75%, of about 40% to about 75%, of about 50% to about 74%, of about 50% to about 73%, of about 50% to about 72%, of about 55% to about 70%, of about 55% to about 68%, of about 58% to about 65%, of about 60% to about 64%, less than 76%, less than 75%, less than about 74%, less than about 73%, less than about 72%, less than about 71%, less than about 70%, less than about 68%, less than about 65%, less than about 64%, less than about 63%, or about 2%, specifically reciting all 0.1% increments within the specified ranges and all ranges formed therein or thereby. All relative humidity measurements were taken according to the Humidity Test herein. A chart of the relative humidity % of commercially available absorbent articles compared to the relative humidity % of an example absorbent article of the present disclosure with a high basis weight topsheet is illustrated in Table 1 below. The WVTR values for the backsheet film of each absorbent article are also illustrated in Table 1 below. It is important to note that even with a higher basis weight topsheet (about 35 gsm in the example), the absorbent article of the present disclosure achieved about the same relative humidity as a commercially available airfelt-free product, namely, Pampers Cruisers, with a low basis weight topsheet (about 15.5 gsm). As a result, the benefit of low relatively humidity is realized in absorbent articles having airfelt-free cores in combination with high basis weight topsheets (e.g., topsheets having a basis weight over 25 gsm).

TABLE 1

| Product (All Size 4) | % RH | WVTR g/m$^2$ day |
|---|---|---|
| Huggies Little Movers (AF/C) TSBW-14.5 gsm | 79 | 5,700 |
| Huggies Snug & Dry (AF/C) TSBW-14.5gsm | 83 | 2,100 |
| Pampers Baby Dry (AF/C) TSBW-15 gsm | 76 | 5,300 |
| Pampers Cruisers (AFF) TSBW-15.5 gsm | 58 | 5,400 |
| Pampers Swaddlers (AFF) TSBW-15.5 gsm | 60 | 4,200 |
| Absorbent Article of the Present Disclosure TSBW-35 gsm; Pampers Cruisers diaper with 35 gsm TSBW (AFF) | 62 | 5,400 |

(AFF)—means the absorbent article has an absorbent core that is substantially cellulose free or cellulose free.
(AF/C)—means the absorbent article has an absorbent core that comprises absorbent polymer particulate material and at least 30% cellulose fibers, by weight of the total absorbent material within the absorbent core.
TSBW—means topsheet basis weight, according to the Basis Weight Test herein.

WVTR

The WVTR, or water vapor transmission rate, of the backsheet films of the tested absorbent articles are illustrated in Table 1 above. The WVTR value specifies how "breathable" or vapor permeable a material, such as a backsheet film is. The higher the WVTR value, the more breathable or vapor permeable a material is, and vice versa. As can be seen, all of the tests diapers had backsheet films that had WVTR values of less than 6,000 g/m$^2$ day, according to the WVTR Test herein. A WVTR value of the absorbent articles of the present disclosure may be less than 7,500 g/m² day, less than 7,000 g/m² day, less than 6,500 g/m² day, less than 6000 g/m² day, less than 5,800 g/m² day, less than 5,500 g/m² day, or less than 5,450 g/m² day, according to the WVTR Test herein. The minimum WVTR value for the backsheet films of the absorbent articles of the present disclosure may be at least 750 g/m² day, at least 1,000 g/m² day, at least 1,500 g/m² day, at least 2,000 g/m² day, at least 2,500 g/m² day, at least 3,000 g/m² day, or at least 3,500 g/m² day, according to the WVTR Test herein. The top and bottom WVTR numbers herein form ranges that are also specifically included in the present disclosure (e.g., 2,000 g/m² day to 6,500 g/m² day).

Method of Relative Humidity Testing

A method of determining a relative humidity level in two different absorbent articles is provided. The method may comprise:

providing a first mannequin comprising a first fluid source (the mannequin is in accordance with the Humidity Test herein);

placing a first absorbent article on the first mannequin (placement is in accordance with the Humidity Test herein), wherein the first absorbent article comprises a substantially airfelt-free core and a wearer-facing surface;

providing a first relative humidity sensor in a first void space between an outer surface of the first mannequin and the wearer-facing surface of the first absorbent article (in accordance with the Humidity Test herein);

applying fluid at about body temperature to the first absorbent article using the first fluid source (the fluid may be applied in gushes, in accordance with the Humidity Test herein);

waiting for a period of time after the fluid is applied to the first absorbent article (in accordance with the Humidity Test herein);

measuring a first relative humidity level within the first void space after the period of time using the first relative humidity sensor (in accordance with the Humidity Test herein);

providing a second mannequin comprising a second fluid source (the mannequin is in accordance with the Humidity Test herein), wherein the second mannequin is substantially the same as the first mannequin;

placing a second absorbent article on the second mannequin (placement is in accordance with the Humidity Test herein), wherein the second absorbent article comprises an absorbent core that comprises at least 25% airfelt by weight of absorbent material within the absorbent core and a wearer-facing surface;

providing a second relative humidity sensor in a second void space between an outer surface of the second mannequin and the wearer-facing surface of the second absorbent article (in accordance with the Humidity Test herein), wherein the second relative humidity sensor is the same as the first relative humidity sensor;

applying the fluid at about body temperature to the second absorbent article using the second fluid source (the fluid may be applied in gushes, in accordance with the Humidity Test herein);

waiting for the period of time after the fluid is applied to the second absorbent article (in accordance with the Humidity Test herein);

measuring a second relative humidity level within the second void space after the period of time using the second relative humidity sensor (in accordance with the Humidity Test herein);

displaying or communicating a first result of the first relative humidity level; and displaying or communicating a second result of the second relative humidity level.

The first absorbent article is substantially the same size as the second absorbent article.

The method comprising positioning the first absorbent article on the first mannequin in substantially the same position on the first mannequin as the second absorbent article is positioned on the second mannequin (placement is in accordance with the Humidity Test herein).

The method may comprise comparing the first result of the first relative humidity level with the second result of the second relative humidity level and communicating the first result and the second result. The communicating may be in the form of indicator lights or signals, or advertising, whether through hard copies, signage, electronic media, and/or other media.

The absorbent core of the second absorbent article may comprise at least 30% airfelt by weight of absorbent material within the absorbent core.

The absorbent core of the second absorbent article may comprise at least 35% airfelt by weight of absorbent material within the absorbent core.

The applying the fluid to the first absorbent article step using the first fluid source comprises applying an amount of fluid based on the size of absorbent article being tested (in accordance with the Humidity Test herein).

The applying the fluid to the second absorbent article using the second fluid source comprises applying an amount of fluid based on the size of absorbent article being tested (in accordance with the Humidity Test herein).

The fluid may comprise a synthetic urine solution or other suitable solution.

The substantially airfelt-free core may comprise less than 3% airfelt by weight of absorbent material within the absorbent core.

The substantially airfelt-free core may comprise less than 1% airfelt by weight of absorbent material within the absorbent core.

A method of determining a relative humidity level in void space defined between a wearer-facing surface of an absorbent article and an outer surface of a mannequin and after one or more simulated urination events is provided. The method may comprise:

providing the mannequin comprising a fluid source (the mannequin is in accordance with the Humidity Test herein);

applying the absorbent article comprising a substantially airfelt-free absorbent core to the mannequin (placement is in accordance with the Humidity Test herein);

providing a relative humidity sensor in the void space (in accordance with the Humidity Test herein);

applying a fluid at about body temperature to the absorbent article using the fluid source (the fluid may be applied in gushes, in accordance with the Humidity Test herein);

waiting for a period of time after the fluid is applied to the absorbent article (in accordance with the Humidity Test herein);

measuring a relative humidity level within the void space after the period of time using the humidity sensor (in accordance with the Humidity Test herein); and displaying a result of the relative humidity level within the void space.

The substantially airfelt-free absorbent core may comprise less than 3% airfelt by weight of absorbent material within the absorbent core.

The substantially airfelt-free absorbent core may comprise less than 1% airfelt by weight of absorbent material within the absorbent core.

The applying the fluid to the absorbent article using the fluid source comprises applying an amount of fluid based on the size of absorbent article being tested (in accordance with the Humidity Test herein).

The fluid may comprise a synthetic urine solution or other suitable fluid.

The method may comprise communicating or advertising the result of the relative humidity level.

The absorbent article specified above is a first absorbent article. The method may further comprise:

removing the first absorbent article from the mannequin;

applying a second absorbent article comprising an absorbent core comprising at least 25% airfelt by weight of absorbent material within the absorbent core to the mannequin at the same position as the first absorbent was positioned on the mannequin (placement is in accordance with the Humidity Test herein), wherein a second void space is created intermediate a wearer-facing surface of the second absorbent article and the outer surface of the mannequin;

applying the fluid at about body temperature to the second absorbent article using the fluid source (the fluid may be applied in gushes, in accordance with the Humidity Test herein);

waiting for the period of time after the fluid is applied to the second absorbent article (in accordance with the Humidity Test herein);

measuring a second relative humidity level within the second void space after the period of time using the humidity sensor positioned within the second void space (in accordance with the Humidity Test herein); and displaying a result of the second relative humidity level within the second void space.

The method may comprise comparing the result of the relative humidity level with the result of the second relative humidity level and communicating or advertising the compared results.

Certain parameter and test results for the below examples are summarized in Table 2 herein below.

Example 1—Comparative Standard Bulky

The 12 gsm spunmelt type nonwoven batt produced online in a continuous process from polypropylene (Mosten NB425 from Unipetrol), where monocomponent polypropylene filaments with a fibre diameter of 18-30 μm (1.5 to 2.5 den) are produced and subsequently collected on a moving belt. To increase strength a patterned calender is used consisting of a pair of heated rollers, where one roller has raised comparative pattern "Standard bulky" (FIG. 4A). The temperature of the calender rollers (smooth roller/patterned roller) is 165° C./168° C. and the pressure is 75 N/mm.

Example 2—Comparative Standard Bulky

A 14 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised comparative pattern "Standard bulky" (FIG. 4A). The temperature of the calender rollers (smooth roller/patterned roller) is 165° C./168° C. and the pressure is 75 N/mm.

Example 3—Comparative Standard Bulky

A 15 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised comparative pattern "Standard bulky" (FIG. 4A). The temperature of the calender rollers (smooth roller/patterned roller) is 168° C./171° C. and the pressure is 75 N/mm.

Example 4—Comparative Standard Bulky

A 17 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised comparative pattern "Standard bulky" (FIG. 4A). The temperature of the calender rollers (smooth roller/patterned roller) is 168° C./171° C. and the pressure is 75 N/mm.

Example 5—Comparative Standard

Figure 4B:
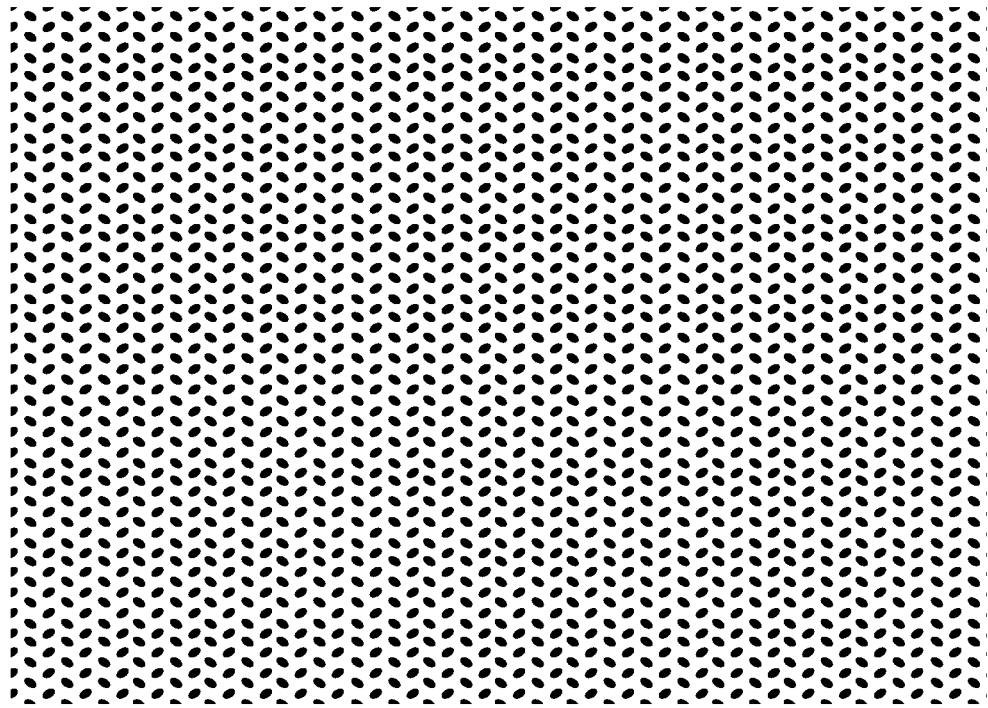
FIG. 4B is a view of another pattern of bonding surface shapes of bonding protrusions that may be imparted to the surface of a calender roller, to create another corresponding pattern of consolidating bond impressions having bond shapes in a nonwoven web.
Figure 4C:
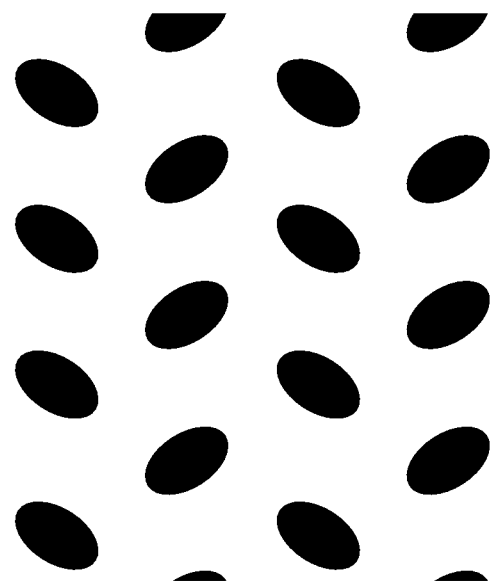
FIG. 4C is a magnified view of the pattern of bonding surface shapes of bonding protrusions or consolidating bond impressions having bond shapes appearing in FIG. 4B.

A 15 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised comparative pattern "Standard" (FIG. 4B). The temperature of the calender rollers (smooth roller/patterned roller) is 170° C./173° C. and the pressure is 95 N/mm.

Example 6—Comparative Standard

A 17 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised comparative pattern "Standard" (FIG. 4B). The temperature of the calender rollers (smooth roller/patterned roller) is 170° C./173° C. and the pressure is 95 N/mm.

Example 7—Comparative Standard

A 15 gsm spunmelt type nonwoven batt, produced using a continuous online process from polypropylene (HH 450 FB from Borelais) and polylactic acid (Ingeo 6202D from NatureWorks), where first the bicomponent core/sheath type filaments are produced, where the core representing 80% is from polylactic acid and the sheath is from polypropylene. The individual filaments a fibre diameter of 18-40 μm are collected on a moving belt. The batt was produced on REICOFIL 3 technology from 1 beam.

To increase strength a patterned calender is used, that consist of a pair of heated rollers, where one roller has raised comparative pattern "Standard" (FIG. 4B). The temperature of the calender rollers (smooth roller/patterned roller) is 140° C./140° C. and the pressure is 75 N/mm.

Example 8—Comparative Standard

The 15 gsm spunmelt type nonwoven batt produced online in a continuous process from a mixture of polypropylene (Mosten NB425 from Unipetrol) and copolymer (Vistamaxx 6102 from Exxon) in the weight ratio 81:19, where monocomponent polypropylene filaments with a fibre diameter of 20-40 μm are produced and subsequently collected on a moving belt. The batt was produced on REICO-FIL 3 technology from 2 beams.

To increase strength a patterned calender is used consisting of a pair of heated rollers, where one roller has raised comparative pattern "Standard" (FIG. 4B). The temperature of the calender rollers (smooth roller/patterned roller) is 145° C./145° C. and the pressure is 75 N/mm.

Example 9—"S" Shape

A 12 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised pattern "S-shape" according to the present disclosure (FIG. 6). The temperature of the calender rollers (smooth roller/patterned roller) is 165° C./168° C. and the pressure is 75 N/mm.

Example 10—"S" Shape

A 14 gsm spunmelt type nonwoven batt produced online in a continuous process from a mixture of polypropylene (Mosten NB425 from Unipetrol) and color masterbatch (Sanylene white PPRC 70 from Clariant) in the weight ratio 99.5:0.5, where monocomponent polypropylene filaments with a fibre diameter of 18-30 μm are produced and subsequently collected on a moving belt. To increase strength a patterned calender is used consisting of a pair of heated rollers, where one roller has raised pattern "S-shape" according to the present disclosure (FIG. 6). The temperature of the calender rollers (smooth roller/patterned roller) is 165° C./168° C. and the pressure is 75 N/mm.

Example 11—"S" Shape

A 15 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised pattern "S-shape" according to the present disclosure (FIG. 6). The temperature of the calender rollers (smooth roller/patterned roller) is 168° C./171° C. and the pressure is 75 N/mm.

Example 12—"S" Shape

A 17 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised pattern "S-shape" according to the present disclosure (FIG. 6). The temperature of the calender rollers (smooth roller/patterned roller) is 168° C./171° C. and the pressure is 75 N/mm.

The strengthened nonwoven web is then subsequently impregnated with a hydrophilic surfactant (Silastol PHP 90 from Schill and Seilacher) using a dip roller (kiss-roll) and dried. The extra weight of the surfactant in dry form is approximately 0.4%.

Example 13—"S" Shape

A 17 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised pattern "S-shape" according to the present disclosure (FIG. 6). The temperature of the calender rollers (smooth roller/patterned roller) is 168° C./171° C. and the pressure is 75 N/mm.

Example 14—"Wing" Shape

A 12 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised pattern "wing-shape" according to the present disclosure (FIG. 5). The temperature of the calender rollers (smooth roller/patterned roller) is 165° C./168° C. and the pressure is 75 N/mm.

Example 15—"Wing" Shape

A 14 gsm spunmelt type nonwoven batt produced online in a continuous process from a mixture of polypropylene (Mosten NB425 from Unipetrol) and color masterbatch (CC10031739BG green from PolyOne) in the weight ratio 99.3:0.7, where monocomponent polypropylene filaments with a fibre diameter of 18-30 μm are produced and subsequently collected on a moving belt. To increase strength a patterned calender is used consisting of a pair of heated rollers, where one roller has raised pattern "S-shape" according to the present disclosure (FIG. 5). The temperature of the calender rollers (smooth roller/patterned roller) is 165° C./168° C. and the pressure is 75 N/mm.

Example 16—"Wing" Shape

A 15 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised pattern "wing-shape" according to the present disclosure (FIG. 5). The temperature of the calender rollers (smooth roller/patterned roller) is 168° C./171° C. and the pressure is 75 N/mm.

Example 17—"Wing" Shape

A 17 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised pattern "wing-shape" according to the present disclosure (FIG. 5). The temperature of the calender rollers (smooth roller/patterned roller) is 168° C./171° C. and the pressure is 75 N/mm.

The strengthened nonwoven web is then subsequently impregnated with a hydrophilic surfactant (Silastol PHP 90 from Schill and Seilacher) using a dip roller (kiss-roll) and dried. The extra weight of the surfactant in dry form is approximately 0.4%.

Example 18—"Wing" Shape

A 17 gsm spunmelt type nonwoven batt produced online in a continuous process from polypropylene (Mosten NB425 from Unipetrol), where monocomponent polypropylene filaments with a fibre diameter of 18-30 μm are produced and subsequently collected on a moving belt. To increase strength a patterned calender is used consisting of a pair of heated rollers, where one roller has raised pattern "wing-shape" according to the present disclosure (FIG. 5). The temperature of the calender rollers (smooth roller/patterned roller) is 168° C./171° C. and the pressure is 75 N/mm.

Example 19—"Wing" Shape

A 15 gsm spunmelt type nonwoven batt, produced using a continuous online process from polypropylene (Mosten NB425 from Unipetrol) and polyethylene (Liten LS87 from Unipetrol), where first the bicomponent core/sheath type filaments are produced, where the core representing 50% is from polypropylene and the sheath is from polyethylene. The individual filaments with a fibre diameter of 18-40 μm are collected on a moving belt.

To increase strength a patterned calender is used, that consist of a pair of heated rollers, where one roller has raised pattern "wing-shape" according to the present disclosure (FIG. 5). The temperature of the calender rollers (smooth roller/patterned roller) is 154° C./154° C. and the pressure is 75 N/mm.

Example 20—"S-Shape v2"

A 25 gsm spunmelt type nonwoven batt, produced using a continuous online process from polypropylene (Mosten NB425 from Unipetrol) and polyethylene (Liten LS87 from Unipetrol), where first the bicomponent side/side type filaments are produced, where the one side representing 50% is from polyethylene and the second side is from polypropylene. The individual filaments with a fibre diameter of 15-25 μm are collected on a moving belt. The batt was produced from two beams REICOFIL 3 technology.

Figure 7:
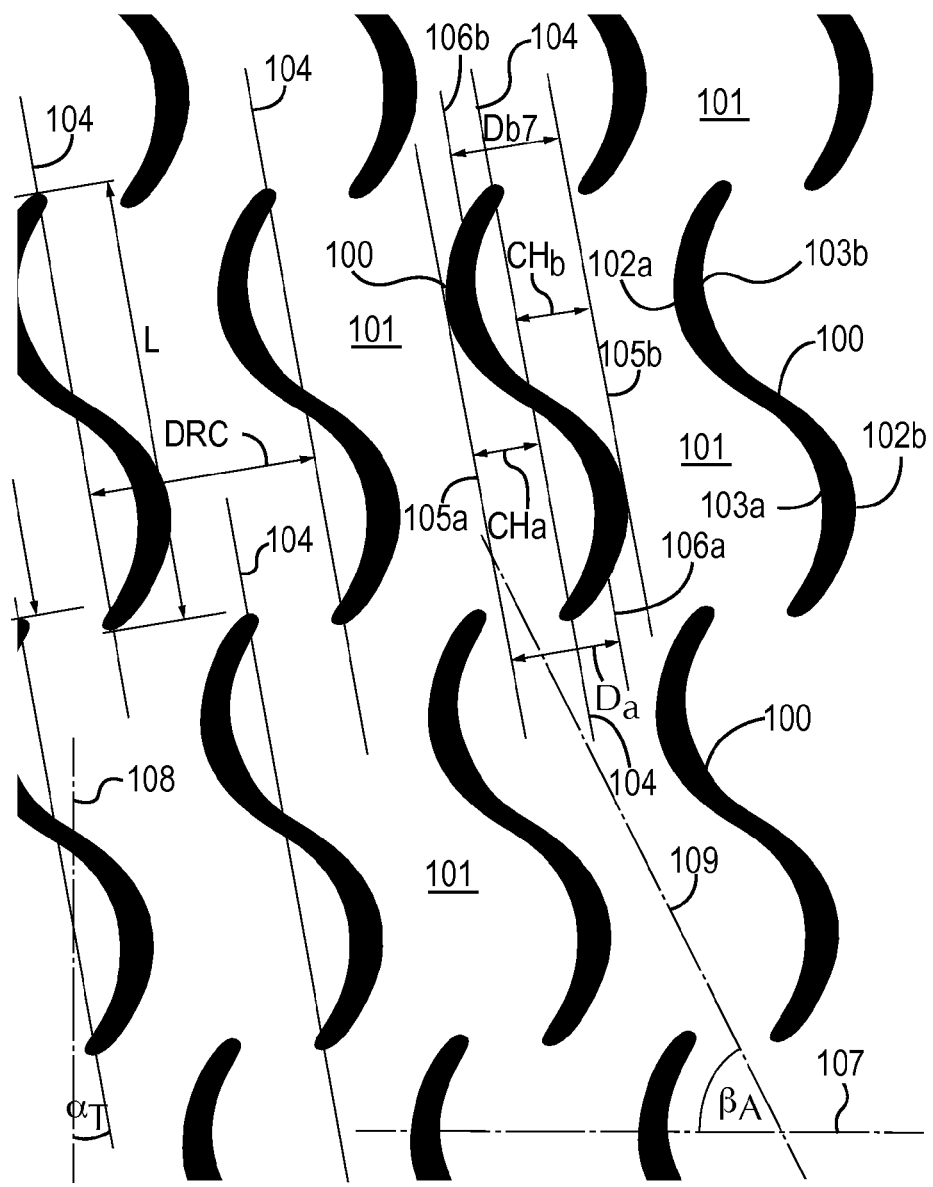
FIG. 7 is a view of another pattern of bonding surface shapes of bonding protrusions that may be imparted to the surface of a calender roller, to create another corresponding pattern of consolidating bond impressions having bond shapes in a nonwoven web.

To increase strength a patterned calender is used, that consist of a pair of heated rollers, where one roller has raised pattern "S-shape v2" (FIG. 7). The temperature of the calender rollers (smooth roller/patterned roller) is 152° C./142° C. and the pressure is 60 N/mm.

Example 21—"S-Shape v2"

A 15 gsm spunmelt type nonwoven batt produced online in a continuous process from polypropylene (Mosten NB425 from Unipetrol), where monocomponent polypropylene filaments with a fibre diameter of 15-25 μm are produced and subsequently collected on a moving belt. The batt was produced from two beams on REICOFIL 3 technology.

To increase strength a patterned calender is used consisting of a pair of heated rollers, where one roller has raised pattern "S-shape v2" according to the present disclosure (FIG. 7). The temperature of the calender rollers (smooth roller/patterned roller) is 150° C./145° C. and the pressure is 70 N/mm.

Example 22—"S-Shape v2"

A 25 gsm spunmelt type nonwoven batt, produced using a continuous online process from polypropylene (Mosten NB425 from Unipetrol) and copolymer (Vistamaxx 6202 from Exxon) in the weight ratio 84:16 where first the monocomponent type filaments are produced. The individual filaments a with a fibre diameter of 15-25 μm are collected on a moving belt. The batt was produced from two beams on REICOFIL 3 technology.

To increase strength a patterned calender is used, that consist of a pair of heated rollers, where one roller has raised pattern "S-shape v2" (FIG. 7). The temperature of the calender rollers (smooth roller/patterned roller) is 158° C./155° C. and the pressure is 70 N/mm.

TABLE 2

| Mes. unit | Pattern | NW | Modified thickness mm | Density kg/m$^3$ | Handle O meter - MD mN | Tensile strength MD/CD ratio — | Strike through time (STT) S |
|---|---|---|---|---|---|---|---|
| Example 1 | Comparative | 12 gsm PP-SSS | 0.21 | 57.1 | 36.0 | 3.07 | >20 |
| Example 2 | standard bulky | 14 gsm PP-SSS | 0.23 | 60.9 | 40.0 | 2.64 | >20 |
| Example 3 | | 15 gsm PP-SSS | 0.24 | 62.5 | 46.6 | 2.50 | >20 |
| Example 4 | | 17 gsm PP-SSS | 0.26 | 65.4 | 61.0 | 2.51 | >20 |
| Example 5 | Comparative | 15 gsm PP-SSS | 0.17 | 88.2 | 48.0 | 2.0 | >20 |
| Example 6 | standard | 17 gsm PP-SSS | 0.20 | 85.0 | 64.0 | 2.0 | >20 |
| Example 7 | | 15 gsm BICO PLA/PP-S | 0.19 | 79.0 | 61.0 | 1.6 | >20 |
| Example 8 | | 15 gsm mono PP + copolymer-SS | 0.20 | 75.0 | 21.2 | 2.3 | >20 |
| Example 9 | "S" shape | 12 gsm PP-SSS | 0.23 | 52.2 | 33.8 | 2.40 | >20 |
| Example 10 | | 14 gsm PP-SSS | 0.26 | 53.8 | 36.5 | 2.14 | >20 |

TABLE 2-continued

| Mes. unit | Pattern | NW | Modified thickness mm | Density kg/m³ | Handle O meter - MD mN | Tensile strength MD/CD ratio | Strike through time (STT) s |
|---|---|---|---|---|---|---|---|
| Example 11 | | 15 gsm PP-SSS | 0.27 | 55.6 | 41.9 | 2.08 | >20 |
| Example 12 | | 17 gsm PP-SSS hydrophilic | 0.29 | 58.6 | 53.9 | 1.99 | 3.3 |
| Example 13 | | 17 gsm PP-SSS | 0.29 | 58.6 | 53.9 | 1.99 | >20 |
| Example 14 | "wing" shape | 12 gsm PP-SSS | 0.22 | 54.5 | 30.4 | 2.76 | >20 |
| Example 15 | | 14 gsm PP-SSS | 0.25 | 56.0 | 34.6 | 2.26 | >20 |
| Example 16 | | 15 gsm PP-SSS | 0.26 | 57.7 | 41.6 | 2.21 | >20 |
| Example 17 | | 17 gsm PP-SSS hydrophilic | 0.29 | 58.6 | 46.0 | 2.21 | 3.2 |
| Example 18 | | 17 gsm PP-SSS | 0.29 | 58.6 | 46.7 | 2.21 | >20 |
| Example 19 | "wing" shape | 15 gsm BICO PP/PE SSS | 0.28 | 53.6 | 30.2 | 2.11 | >20 |
| Example 20 | "S" shape v2 | 25 gsm BICO PP/PE side/side-SS | 0.39 | 69.4 | 53.0 | 1.90 | >20 |
| Example 21 | "S" shape v2 | 15 gsm PP-SS | 0.29 | 53.6 | 44.1 | 1.81 | >20 |
| Example 22 | "S" shape v2 | 25 gsm PP + copolymer-SS | 0.37 | 74.0 | 56.3 | 1.93 | >20 |

Packages

Absorbent articles of the present disclosure may be placed into packages. The packages may comprise polymeric films and/or other materials. Graphics or indicia relating to properties of the absorbent articles may be formed on, positioned on, and/or placed on outer portions of the packages. Each package may comprise one or more absorbent articles. The absorbent articles may be packed under compression so as to reduce the size or height of the packages while still providing an adequate amount of absorbent articles per package.

Accordingly, packages of the absorbent articles according to the present disclosure may have an in-bag stack height of less than about 105 mm, less than about 100 mm, less than about 95 mm, less than about 90 mm, less than about 85 mm, less than about 90 mm, but greater than 75 mm, less than about 85 mm, but greater than 75 mm, less than about 80 mm, less than about 78 mm, or less than about 76 mm, according to the In-Bag Stack Height Test described herein. Alternatively, packages of the absorbent articles of the present disclosure may have an in-bag stack height of from about 70 mm to about 100 mm, from about 70 mm to about 90 mm, from about 75 to about 90 mm, from about 75 to about 85 mm, from about 72 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

These packages of the absorbent articles of the present disclosure with reduced in-bag stack heights compared to conventional absorbent article packages provide caregivers with packages that are convenient to handle and store, while also providing manufacturers with significant distribution savings because of the smaller package sizes.

Further details regarding in-back stack height are disclosed in U.S. Pat. No. 8,585,666, to Weisman et al., issued on Nov. 19, 2013.

Test/Measurement Methods

Basis Weight

The "basis weight" of a nonwoven web is measured according to the European standard test EN ISO 9073-1: 1989 (conforms to WSP 130.1). The nonwoven web to be measured is removed from an absorbent article using a cryogenic freeze spray (e.g. Cytofreeze) from ten (10) replicate absorbent articles. Each of the nonwoven webs is then cut to a test specimen size of at least 100 cm² and their mass measured to the nearest 0.1 mg. Basis weight is calculated as mass per unit area.

Thickness

The "thickness" of a nonwoven web is measured according to the European standard test EN ISO 9073-2:1996 (conforms to WSP 120.6) with following modification: the overall weight of upper arm of the machine including added weight is 130 g.

MD/CD Ratio

The "MD/CD ratio" is the ratio of material's tensile strength at peak in the MD and CD direction. Both were measured according to the EDANA standard method WSP 110.4-2005, where sample width is 50 mm, jaw distance is 100 mm, speed 100 mm/min and preload 0.1N.

MD/CD ratio=tensile strength at peak in MD[N/5 cm]/tensile strength at peak in CD[N/5 cm]

Softness

The "softness" of a nonwoven web may be measured using to the "Handle-O-Meter" test. The test used herein is the INDA IST 90.3-01. The lower the value, the softer is the web.

Density

The "density" is the ratio of basis weight and thickness and indicates the bulkiness and fluffiness of the product, which are important qualities of the nonwoven web according to the present disclosure. The lower the value, the bulkier is the web.

Density [kg/m³]=basis weight [g/m²]/thickness [mm].

Hydrophilic Properties

The "hydrophilic properties" of a nonwoven web may be measured using the "Strike Through Time" test. The test used herein is the EDANA standard test WSP 70.3-2005 The lower the value, the more hydrophilic is the web.

Opacity

The opacity of a material is the degree to which light is blocked by that material. A higher opacity value indicates a higher degree of light block by the material. Opacity may be measured using a 0° illumination/45° detection, circumferential optical geometry, spectrophotometer with a computer interface such as the HunterLab LabScan XE running Universal Software (available from Hunter Associates Laboratory Inc., Reston, Va.). Instrument calibration and measurements are made using the standard white and black calibration plates provided by the vendor. All testing is performed in a room maintained at about 23±2° C. and about 50±2% relative humidity.

Configure the spectrophotometer for the XYZ color scale, D65 illuminant, 10° standard observer, with UV filter set to nominal. Standardize the instrument according to the manufacturer's procedures using the 1.20 inch port size and 1.00 inch area view. After calibration, set the software to the Y opacity procedure.

To obtain the specimen, lay the sample flat on a bench, body facing surface downward, and measure the total longitudinal length of the article. Note a site 33% of the total length from the front waist of the article along the longitudinal axis and a second site, 33% of the total length from the back waist of the article. Carefully remove the backsheet laminate, consisting of both the film and nonwoven web, from the garment-facing side of the article. A cryogenic spray, such as Cyto-Freeze (obtained from Control Company, Houston, Tex.), may be used to separate the backsheet laminate from the article. Cut a piece 50.8 mm by 50.8 mm centered at each site identified above. Precondition samples at about 23° C.±2° C. and about 50%±2% relative humidity for 2 hours prior to testing.

Place the specimen over the measurement port. The specimen should completely cover the port with the surface corresponding to the garment-facing surface of the article directed toward the port. Cover the specimen with the white standard plate. Take a reading, then remove the white tile and replace it with black standard tile without moving the specimen. Obtain a second reading, and calculate the opacity as follows:

$$\text{Opacity} = Y \text{ value}_{(black\ backing)} / Y \text{ value}_{(white\ backing)} \times 100$$

A total of five identical articles are analyzed and their opacity results recorded. Calculate and report the average opacity and standard deviation for the 10 backsheet laminate measurements to the nearest 0.01%.

Using the same specimens as above, remove the nonwoven web from the film layer for analysis. The cryogenic spray can once again be employed. Precondition samples at about 23° C.±2° C. and about 50%±2% relative humidity for 2 hours prior to testing. In like fashion, analyze the nonwoven web layer following the above procedure. Calculate and report the average opacity and standard deviation for the 10 nonwoven web measurements to the nearest 0.01%.

Bond Shape Measurement Methods

Area, distance and angle measurements are performed on images generated using a flat bed scanner capable of scanning at a resolution of at least 4800 dpi in reflectance mode (a suitable scanner is the Epson Perfection V750 Pro, Epson, USA). Measurements are performed using ImageJ software (Version 1.43u, National Institutes of Health, USA) and calibrated against a ruler certified by NIST.

Samples of the subject nonwoven web that are 80 mm by 80 mm are used. Precondition the samples at about 23° C.±2° C. and about 50%±2% relative humidity for 2 hours prior to testing. Identify the machine direction of the nonwoven web and draw a fine line on each sample along the machine direction to enable scanned images to be aligned.

Place the sample to be measured on the flat bed scanner, with the surface bearing the bond impressions or bond shapes facing downward, with the ruler directly adjacent. Placement is such that the dimension corresponding to the machine direction of the nonwoven is parallel to the ruler. A black backing is placed over the specimen and the lid to the scanner is closed. Acquire an image composed of the nonwoven and ruler at 4800 dpi in reflectance mode in 8 bit grayscale and save the file. Open the image file in ImageJ and perform a linear calibration using the imaged ruler.

Unless otherwise stated, dimensional and area measurements are made in triplicate, of three similar bond shapes on each sample for 6 similar samples. The 18 values are averaged and reported.

Not intending to be bound by the specific examples, FIGS. 5A through 6B are referenced to illustrate the following dimension measurements. These measurement methods are equally applicable to other bond shapes and repeating bond patterns.

Greatest Measurable Length (L)

The bond shape has a perimeter and a greatest measurable length. Identify a shape length line (e.g. line 104) which intersects the two farthest-most points along the perimeter. Draw a shape length line through these points. With the measuring tool, measure the length along the line segment between these points to the nearest 0.001 mm. For example, the greatest measurable lengths in FIGS. 5B and 6B are indicated at L, respectively measured along shape length lines 104.

Greatest Measurable Width (W)

Relative the greatest measurable length, the bond shape has a greatest measurable width measured along a direction perpendicular to the shape length line. Draw two lines, parallel to the shape length line, and tangent to the bond shape perimeter at one or more outermost points that are most distant from the shape length line. These are the shape width lines. With the measuring tool, measure the greatest measurable width between the shape width lines along a line segment perpendicular to the shape length line to the nearest 0.001 mm. For example, the greatest measurable widths in FIGS. 5B and 6B are indicated at W, respectively measured between lines 105$a$ and 105$b$ perpendicular to shape length lines 104.

Minimum Passageway Clearance

Any two adjacent bond shapes have minimum passageway clearance, defined as the smallest measurable distance therebetween. Identify the two parallel lines, one tangent to the perimeter of the first shape where it appears closest to the second shape, and one tangent to the perimeter of the second shape where it appears closest to the first shape, that lie closer together than any other such parallel lines that can be identified. The minimum passageway clearance is the distance between the identified parallel lines, measured along a line perpendicular to them.

Camber Height (CH)

If the bond shape has a perimeter with a convex portion, the convex portion has a maximum distance from the shape length line, referred to herein as the camber height. Draw a line that is tangent to the convex portion, and parallel to the shape length line. With the measuring tool, measure the distance between width between this tangent line and the shape length line along a direction perpendicular to the shape length line, to the nearest 0.001 mm. For example, the camber heights of the convex portions in FIGS. 5B and 6B are CH, and $CH_a$ and $CH_b$, respectively.

Concavity Depth (D)

If the bond shape has a perimeter with a concave portion, the concave portion has a maximum distance from the facing shape width line. Draw a line that is tangent to the deepest point along the concave portion of the profile, and parallel to the shape length line. This is the shape concavity line. With the measuring tool, measure the distance between shape concavity line and the shape length line along a direction perpendicular to the shape length line to the nearest 0.001 mm. For example, the concavity depths of the concave portions in FIGS. 5B and 6B are D, and $D_a$ and $D_b$, respectively.

Shape Tilt Angle ($\alpha_T$)

The bond shape is rotationally oriented relative the machine direction by shape tilt angle $\alpha_T$. Draw a line in the cross direction, intersecting the shape length line. Draw a line in the machine direction perpendicular to the cross direction line, intersecting both the cross direction line and the shape length line. Using the angle measuring tool, measure the smaller angle between the machine direction line and the shape length line to the nearest 0.1 degree. For example, the angle between lines 108 and 104 in FIG. 5B is the shape tilt angle $\alpha_T$.

Pattern Tilt Angle ($\gamma_P$)

The bond shapes may form a pattern that is tilted from the machine direction by the angle $\gamma_P$. Identify a repeating series of bond shapes in a column. Draw a column line that is tangent on one side at the same position on two similar shapes having similar rotational orientations in the column. Draw a line in the machine direction that intersects this column line at an angle, if such a line exists. With the angle measuring tool, measure the smaller angle between the column line and the machine direction line to the nearest 0.1 degree.

Airflow Restriction Ratio

The bond shapes form a pattern that identifies a maximum airflow restriction by the corresponding bonding roller at the nip. Identify a repeating series of bond shapes lying in a row. Draw a line in the cross direction which intersects these bond shapes at the position relative the machine direction where the shapes occupy the greatest proportion of the distance along the cross direction line. It will be appreciated that it may be necessary to take measurements along several cross direction lines to empirically and/or iteratively identify the one along which the bond shapes occupy the greatest proportion of the distance. With the measuring tool, measure the length from the start of the repeating series to the corresponding location at the end of the repeating series (including distances between bonding shapes) to the nearest 0.001 mm. This is the repeat length in the cross direction. With the measuring tool, measure each of the lengths of the line segments on the cross direction line that lie over the bond shapes, to the nearest 0.001 mm. Add the lengths of all of these line segments within the repeat length, and divide the total by the repeat length. Report to the nearest 0.001. This is the airflow restriction ratio. For example, in FIG. 5C, the repeat length $w_p$ is measured along the cross direction line 107a. The line segments lying over the bond shapes are $w_1$ through $w_4$. The airflow restriction ration is the sum of lengths $w_1$ through $w_4$ divided by the repeat length $w_p$.

Cross-nip Airflow Angle ($\beta_A$)

The bond pattern may provide an airflow path that has a machine direction vector component. Draw a line in the cross direction. Identify a line that can be drawn that extends past at least eight rows of bond shapes without intersecting a bond shape, if such a line exists. This is the cross-nip airflow line. Extend this line to intersect the cross direction line. Using the angle measurement tool, measure the smaller angle between the cross direction line and the airflow line and report to the nearest 0.1 degree. For example, lines 109 in FIGS. 5A and 109 in FIG. 6A are cross-nip airflow lines which intersect the cross direction lines 107 to form the cross-nip airflow angles $\beta_A$.

Bond Area Percentage

Identify a single repeat pattern of bond shapes and areas between them and enlarge the image such that the repeat pattern fills the field of view. In ImageJ, draw a rectangle that circumscribes the repeat pattern. Calculate area of the rectangle and record to the nearest 0.001 mm². Next, with the area tool, trace the individual bond shapes or portions thereof that are entirely within the repeat pattern/rectangle and calculate and add the areas of all bond shapes or portions thereof that are within the repeat pattern/rectangle. Record to the nearest 0.001 mm². Calculate as follows:

Bond Area %=(Sum of areas of bond shapes within repeat pattern)/(total area of repeat pattern)× 100%

Repeat for a total of three non-adjacent regions randomly selected across the sample. Record as Percent Bond Area to the nearest 0.01%. Calculate the average and standard deviation of all 18 of the bond area percentage measurements and report to the nearest 0.01%.

Average Individual Bond Area

Enlarge the image of a region of the sample such that edges of a bond shape can be identified. With the area tool, manually trace the perimeter of a bond. Calculate and record the area to the nearest 0.001 mm². Repeat for a total of five non-adjacent bonds randomly selected across the total sample. Measurements are made on each sample. A total of six samples are measured. Calculate the average and standard deviation of all 30 bond area measurements and report to the nearest 0.001 mm².

Article Measurements

Where measurement of dimensions of an assembled absorbent article (such as a diaper) or features thereof are required, such as, e.g., to calculate area of a surface, the article is laid out on a flat surface, and the article is drawn out longitudinally and laterally to the extent required to remove any slack in the backsheet or other outermost, outward-facing layer, that is present as a result of, e.g., folds, wrinkles or the presence of elastic members.

Compression Loft; Coefficients of Friction

Specimen Preparation (Backsheet Nonwoven Web)

To obtain the specimen, lay the sample diaper flat on a bench, wearer-facing surface downward, and measure the total longitudinal length of the article. Mark a first site on the backsheet that is 33% of the total length from the front waist of the article along its longitudinal axis, and a second site that 33% of the total length from the back waist of the article along the longitudinal axis. Carefully remove a portion of the nonwoven web layer from the backsheet of sufficient size to yield the specimens. A cryogenic spray, such as CYTO-FREEZE (Control Company, Houston, Tex.), may be used to deactivate adhesives and enable easy separation of the nonwoven web layer from the underlying film layer. Cut two square specimens from the removed nonwoven web layer 65 mm by 65 mm each centered at one of the sites identified above, with their cut edges parallel and perpendicular, respectively, with the longitudinal axis of the diaper. Precondition the specimens at about 23° C.±2° C. and about 50%±2% relative humidity for 2 hours prior to testing.

(Topsheet Nonwoven Web)

To obtain the specimen, lay the sample diaper flat on a bench, outward-facing surface downward, and measure the total longitudinal length of the article. Mark a first site on the topsheet that is 33% of the total length from the front waist of the article along its longitudinal axis, and a second site that 33% of the total length from the back waist of the article along the longitudinal axis. Separate the nonwoven web material forming the uppermost layer of the topsheet from any adhered underlying layers, using freeze spray if necessary to deactivate any adhesives. Cut two square specimens from the topsheet nonwoven web material 65 mm by 65 mm each centered at one of the sites identified above, with their cut edges parallel and perpendicular, respectively, with the longitudinal axis of the diaper. Precondition the specimens at about 23° C.±2° C. and about 50%±2% relative humidity for 2 hours prior to testing.

Compression Loft

Compression caliper measurements are performed using an Ono Sokki digital caliper (GS-503 Linear Gauge Sensor with DG-3610 Digital Gauge, Ono Sokki Co, Japan or equivalent) capable of measuring to the nearest 0.01 mm. The circular foot's diameter is 50.8 mm and the applied pressure is 0.5 kPa. The caliper is first zeroed by placing the foot directly on the anvil and setting the digital gauge to zero. The foot is then raised and the first specimen is placed onto the caliper anvil, with the body facing surface directed downward with the first test specimen centered under the foot. The foot is lowered at about 5 mm/sec until it rests on the specimen. Readings are taken after a residence time of 5 sec and recorded to the nearest 0.01 mm. The foot is raised and the measurement is repeated on the second specimen. A total of 10 substantially identical samples are tested and the average of all 20 caliper measurements reported as low compression caliper to the nearest 0.01 mm.

The measurement apparatus is then reconfigured such that the circular foot's diameter is 50.8 mm and the applied pressure is 4.14 kPa. The caliper is first zeroed by placing the foot directly on the anvil and setting the digital gauge to zero. The foot is then raised and the first specimen is placed onto the caliper anvil, with the body facing surface directed downward with the first specimen centered under the foot. The foot is lowered at about 5 mm/sec until it rests on the specimen. Readings are taken after a residence time of 5 sec and recorded to the nearest 0.01 mm. The foot is raised and the measurement is repeated on the second specimen. A total of 10 substantially identical samples are tested and the average of all 20 caliper measurements reported as high compression caliper to the nearest 0.01 mm.

The Compression Loft is calculated as [(low compression caliper)−(high compression caliper)]/(low compression caliper)×100%.

Coefficients of Friction

The static and kinetic coefficients of friction can be measured using ASTM Method D 1894-01 with the following particulars. The test is performed on a constant rate of extension tensile tester with computer interface (a suitable instrument is the MTS Alliance using Testworks 4 Software, as available from MTS Systems Corp., Eden Prarie, Minn.) fitted with a coefficient of friction fixture and sled as described in D 1894-01 (a suitable fixture is the Coefficient of Friction Fixture and Sled available from Instron Corp., Canton, Mass.). The apparatus is configured as depicted in FIG. 1c of ASTM 1894-01 using a stainless steel plane with a grind surface of 320 granulation as the target surface. A load cell is selected such that the measured forces are within 10% to 90% of the range of the cell. The tensile tester is programmed for a crosshead speed of 127 mm/min, and a total travel of 130 mm. Data is collected at a rate of 100 Hz.

The specimen is cut down to a reduced size of 63.5 mm×63.5 mm (again, with cut edges parallel and perpendicular, respectively, with the longitudinal axis of the diaper) and mounted onto the foam rubber side of the sled using double sided adhesive tape (tape should be wide enough to cover 100% of the sled's surface). The specimen is oriented on the sled such that the wearer-facing surface, or outward-facing surface (as on the diaper, according to whether the specimen was taken from topsheet or backsheet) will face the target surface, and the longitudinal orientation of the specimen, relative the longitudinal axis of the diaper, is parallel to the pull direction of the sled. The mass of the sled with mounted sample is recorded to 0.1 gram. The target surface of the stainless steel plane is cleaned with isopropanol before each test.

The static and kinetic coefficients of friction (COF) for the specimen are calculated as follows:

Static COF=$A_S/B$ $A_S$=maximum peak force in grams force (gf) for the initial peak
B=mass of sled in grams Kinetic COF=$A_K/B$ $A_K$=average peak force in grams force (gf) between 20 mm and 128 mm
B=mass of sled in grams In-Bag Stack Height Test The in-bag stack height of a package of the absorbent articles of the present disclosure is determined as follows:

Equipment

Universal Diaper Packaging Tester (UDPT) (Model #M-ROEL; Machine #MK-1071), including a horizontal sliding plate (horizontal plate that moves up and down in a vertical plane) for adding weights. It is counter-balanced by a suspended weight to assure that no downward force is added from the horizontal sliding plate assembly to the diaper package at all times. The UDPT is available from Matsushita Industry Co. LTD, 7-21-101, Midorigaoka-cho, Ashiya-city, Hyogo JAPAN. Zip code: 659-0014. A 850 g (+/−0.5 g) weight.

Definitions

Figure 8:
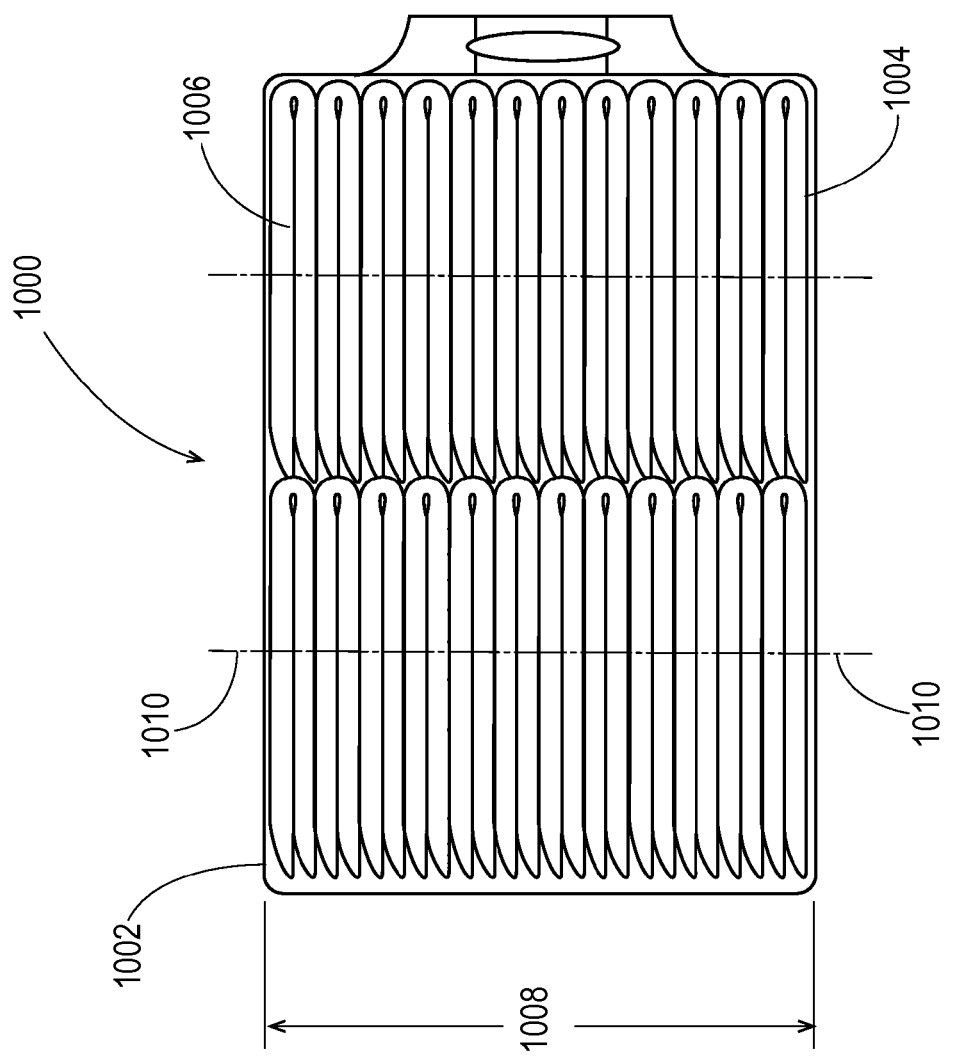
FIG. 8 is a side view of a package of diapers showing the package width. The outer surface is illustrated as transparent for purposes of clarity.

As illustrated in FIG. 8, a package 1000 defines an interior space 1002 and comprises a plurality of absorbent articles 1004. The absorbent articles are in a stack 1006. The package has a package width 1008. The package width 1008 is defined as the maximum distance between the two highest bulging points along the same compression stack axis 1010 of the absorbent article package 1000.

In-Bag Stack Height=(Package Width/Pad Count Per Stack)×10 absorbent articles.

Apparatus Calibration

Pull down the horizontal sliding plate until its bottom touches the tester base plate.
Set the digital meter located at the side of the horizontal sliding scale to zero mark.
Raise the horizontal sliding plate away from the tester base plate.

Test Procedure

Put one of the side panels of the absorbent article package along its width standing at the center of the tester base plate. Make sure the vertical sliding plate (vertical plate that moves left and right in a horizontal plane) is pulled to the right so it does not touch the package being tested.
Add the 850 g weight onto the vertical sliding plate.
Allow the horizontal sliding plate to slide down slowly until its bottom lightly touches desired highest point of the package.
Measure the package width in mm (distance from the top of the base plate to the top of the diaper package).
Record the reading that appears on the digital meter.
Remove the 850 g weight.

Raise the horizontal sliding plate away from the diaper package.
Remove the absorbent article package.
Calculation/Reporting
Calculate and report the "In-Bag Stack Height"=(Package Width/Pad Count Per Stack)×10. Report Sample Identification, i.e. complete description of product being tested (product brand name/size).
Report the determined value for each width measurement to the nearest 1 mm. At least five absorbent article packages having the same pad count are measured in this manner for a given product and the in-bag stack height values are aggregated to calculate an average and standard deviation. Report the Production Date of the measured package (taken from package coding).
Report the Testing Date and Analytical Method used.

Humidity Test

Relative humidity within a diaper is measured on a heated mannequin with dimensions based on ASTM D 4910-02. The testing is performed in a laboratory strictly maintained at 23° C.±2° C. and 50%±2% relative humidity. A sensor that measures both temperature and relative humidity is used to monitor conditions inside the front of the diaper during loading with heated saline solution and the relative humidity is recorded for four hours.

Figures 9, 10:
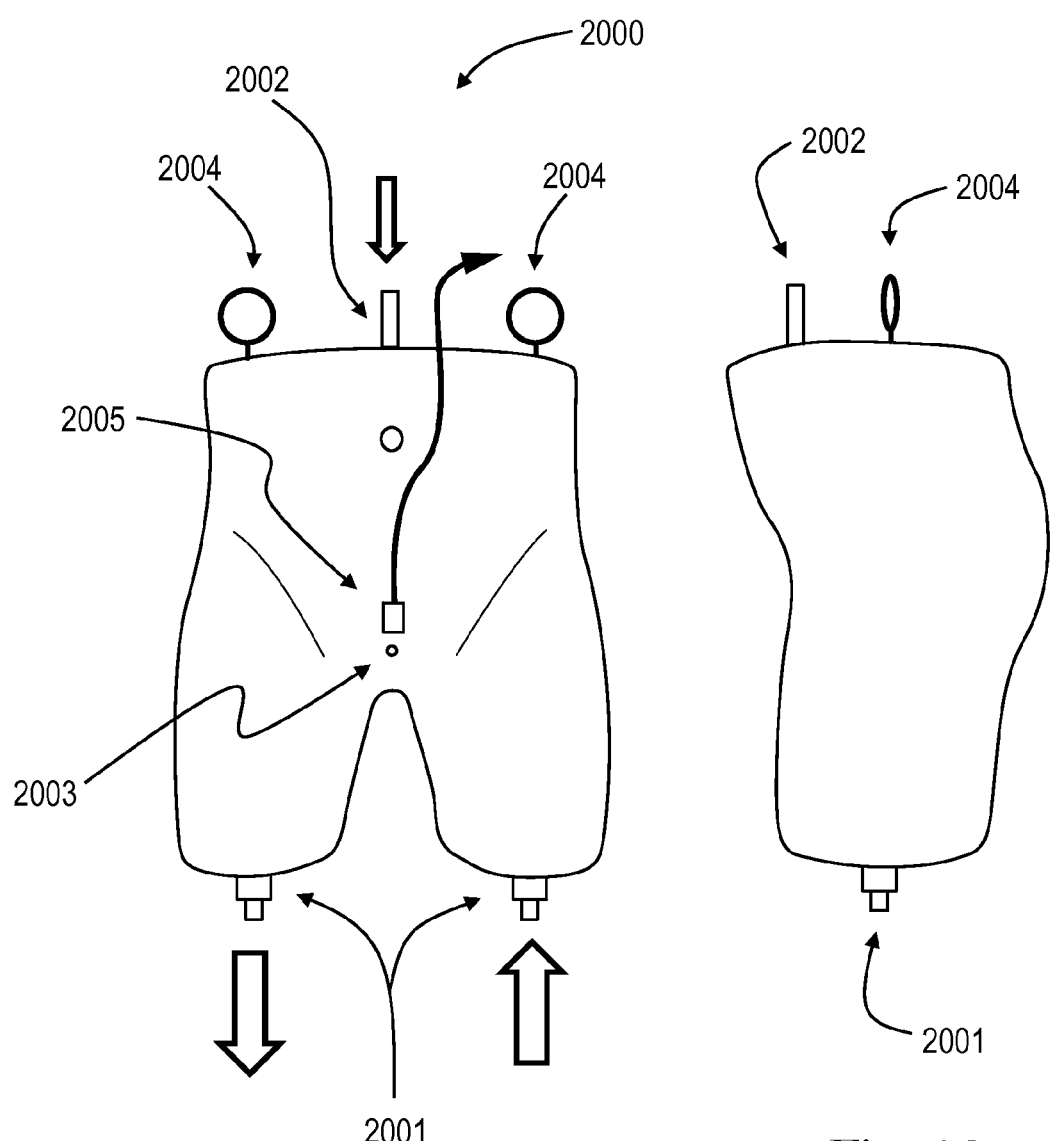
FIG. 9 is a front view of a mannequin used in the Humidity Test herein.
FIG. 10 is a side view of the mannequin of FIG. 9.

Hollow resin-cast hard shell mannequins are made to the waist, hip and thigh girth dimensions as described in ASTM D 4910-02 and summarized in Table 3 below. Referring to FIGS. 9 and 10, the mannequin 2000 is plumbed with quick disconnects fittings 2001 at the bottom of both legs (right side in, left side out) to allow for the circulation of heated water through the internal volume of the mannequin. A heated circulation bath (13 liter capacity, capable of maintaining the temperature to ±0.5)° C. is used to control the temperature of the mannequin. A ⅛ in. stainless steel delivery tube 2002 is internally plumbed entering in the top of the mannequin and exiting at a site 2003 consistent with a male pee point. At the top of the mannequin, two circular fixtures 2004 are attached from which the mannequin can be suspended in a standing position during testing. For convenience the mannequin can be placed on a bench top to apply the diaper and then hung for the test.

A suitable humidity/temperature sensor 2005 is available from Sensirion as Model SHT21, Model EK-H4 multiplex box and Model EK-H4 data logger software. The sensor itself is protected from liquid contact by a Model SF2 filter cap. A sensor with equivalent performance and comparable size can be substituted. The sensor 2005 is attached to the front of the mannequin approximately 10 mm above the site 2003, with its thin flat cable (shown as a dark arrow in FIG. 9) routed along the surface and exiting out the top of the waist.

Diapers are conditioned outside of their packaging in a room maintained at about 23° C.±2° C. and about 50%±2% relative humidity for 24 hours prior to testing. The circulation baths are set to maintain a temperature of 37° C.±2° C. at the sensor 2005. After the temperature has stabilized, the conditioned diaper is fitted onto the mannequin assuring that the waist of the diaper is snug around the mannequin's waist and cuffs are positioned as they would be fitted on a wearer. The diaper is allowed to stabilize on the heated mannequin for an additional 1 hour.

A synthetic urine solution of 0.9% NaCl (w/v) is used for dosing the diaper. A reservoir of the 0.9% saline solution is heated to 38° C.±1° C. in a heated water bath. Using a peristaltic pump, a size dependent dose, as defined in Table 3 below, of 0.9% saline is introduced through the delivery tube 2002 at a rate also defined in Table 3 below. At five minute intervals, two additional doses are delivered in like fashion. After the three doses are complete, the relative humidity is monitored for four (4) hours. Relative Humidity (%) data is recorded at a rate of 1 reading per minute to the nearest 0.1% throughout the experiment. The Relative Humidity (%) is reported as the reading taken at the 4 hour point and recorded to the nearest 0.1%. A total of nine (9) replicate diapers are run in like fashion and their average is reported to the nearest 1%.

TABLE 3

| Diaper Size | ASTM Infant Size | Waist Girth cm | Hip Girth cm | Thigh Girth Cm | Single Dose Volume mL | Delivery Flow Rate mL/s |
|---|---|---|---|---|---|---|
| 1 | 3-6 | 47.0 | 45.7 | 25.1 | 24 | 8 |
| 2 | 6-9 | 47.6 | 47.0 | 25.9 | 24 | 8 |
| 3 | 9-12 | 48.3 | 48.3 | 26.7 | 50 | 10 |
| 4 | 12-18 | 49.5 | 50.8 | 28.3 | 75 | 15 |
| 5 | 18-24 | 50.8 | 53.3 | 29.8 | 75 | 15 |

Water Vapor Transmission Rate (WVTR) Test

The Mocon method is WSP 70.5 for WVTR. Values are reported in units of $g/m^2$ day.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A disposable diaper, comprising:
 a topsheet comprising a first nonwoven web, wherein the topsheet has a basis weight greater than 25 gsm, determined according to the Basis Weight Test as disclosed herein, and wherein the first nonwoven web has a compression loft of at least 30%, determined according to the Compression Loft Test as disclosed herein;
 a backsheet comprising a second nonwoven web and a film, wherein the film has a WVTR value of less than 6,500 $g/m^2$ day, determined according to the WVTR Test as disclosed herein;

an absorbent core comprising an absorbent particulate polymer material disposed between the topsheet and the backsheet, wherein the absorbent core is substantially cellulose free;

wherein the disposable diaper has a relative humidity of less than 74%, after insults of a synthetic urine solution are applied to the diaper, determined according to the Humidity Test as disclosed herein.

2. The disposable diaper of claim 1, wherein the disposable diaper has a relative humidity of less than 70%, after the insults of the synthetic urine solution are applied to the diaper, determined according to the Humidity Test as disclosed herein.

3. The disposable diaper of claim 1, wherein the disposable diaper has a relative humidity of less than 65%, after the insults of the synthetic urine solution are applied to the diaper, determined according to the Humidity Test as disclosed herein.

4. The disposable diaper of claim 1, wherein the disposable diaper has a relative humidity in the range of about 50% to about 70%, after the insults of the synthetic urine solution are applied to the diaper, determined according to the Humidity Test as disclosed herein.

5. The disposable diaper of claim 1, wherein the topsheet has a basis weight greater than 30 gsm, determined according to the Basis Weight Test as disclosed herein.

6. The disposable diaper of claim 1, wherein the topsheet has a basis weight greater than 35 gsm, determined according to the Basis Weight Test as disclosed herein.

7. The disposable diaper of claim 1, wherein the topsheet has a basis weight in the range of about 26 gsm to about 45 gsm, determined according to the Basis Weight Test as disclosed herein.

8. The disposable diaper of claim 1, comprising an acquisition/distribution system positioned at least partially intermediate the topsheet and the absorbent core, wherein the acquisition/distribution system comprises a first layer comprising a nonwoven material having a basis weight greater than about 40 gsm, determined according to the Basis Weight Test as disclosed herein.

9. The disposable diaper of claim 8, wherein the acquisition/distribution system comprises a second layer comprising cross-linked cellulose fibers.

10. The disposable diaper of claim 1, wherein the first nonwoven web has apertures defined therethrough.

11. The disposable diaper of claim 1, wherein the first nonwoven web has a three-dimensional texture defined therein.

12. The disposable diaper of claim 1, wherein the first nonwoven web forms at least 50 percent of a wearer-facing planar surface area of the diaper as defined and circumscribed by an outer profile of the diaper.

13. The disposable diaper of claim 1, wherein the first nonwoven web has a static coefficient of friction equal to or less than 0.4.

14. The disposable diaper of claim 1, wherein the first nonwoven web has a kinetic coefficient of friction equal to or less than 0.35.

15. The disposable diaper of claim 1, wherein the first nonwoven web comprises crimped fibers.

16. The disposable diaper of claim 15, wherein the crimped fibers comprise multicomponent fibers, and wherein the multicomponent fibers have at least two polymer components having differing properties and disposed in either side-by-side configuration or eccentric core/sheath configuration.

17. The disposable diaper of claim 1, wherein the absorbent core comprises:
a first substrate;
a second substrate; and
a thermoplastic adhesive material disposed on or within the absorbent particulate polymer material;
wherein the absorbent particulate polymer material is disposed intermediate the first and second substrates.

18. A package comprising a plurality of the disposable diapers of claim 1, wherein the package has an in-bag stack height of less than 85 mm, determined according to the In-Bag Stack Height Test as disclosed herein.

19. A disposable diaper, comprising:
a topsheet comprising a first nonwoven web, and wherein the first nonwoven web has a compression loft of at least 30%, determined according to the Compression Loft Test as disclosed herein;
a backsheet comprising a second nonwoven web and a film, wherein the second nonwoven web forms a portion of an outermost layer of the diaper, and wherein the film has a WVTR value of less than 6,500 $g/m^2$ day, determined according to the WVTR Test as disclosed herein; and
an absorbent core comprising an absorbent particulate polymer material disposed between the topsheet and the outermost layer, wherein the absorbent core is substantially cellulose free;
wherein the first nonwoven web and the second nonwoven web have a combined basis weight of at least 40 gsm, determined according to the Basis Weight Test as disclosed herein; and
wherein the disposable diaper has a relative humidity of less than 70%, after insults of a synthetic urine solution are applied to the diaper, determined according to the Humidity Test as disclosed herein.

20. The disposable diaper of claim 19, wherein the disposable diaper has a relative humidity of less than 68%, after the insults of the synthetic urine solution are applied to the diaper, determined according to the Humidity Test as disclosed herein.

21. The disposable diaper of claim 19, wherein the disposable diaper has a relative humidity of less than 65%, after the insults of the synthetic urine solution are applied to the diaper, determined according to the Humidity Test as disclosed herein.

22. The disposable diaper of claim 19, wherein the disposable diaper has a relative humidity in the range of about 50% to about 70%, after the insults of the synthetic urine solution are applied to the diaper, determined according to the Humidity Test as disclosed herein.

23. The disposable diaper of claim 19, wherein the first nonwoven web and the second nonwoven web have a combined basis weight of at least 45 gsm, determined according to the Basis Weight Test as disclosed herein.

24. The disposable diaper of claim 19, wherein the first nonwoven web and the second nonwoven web have a combined basis weight of at least 50 gsm, determined according to the Basis Weight Test as disclosed herein.

25. The disposable diaper of claim 19, wherein the first nonwoven web and the second nonwoven web have a combined basis weight of at least 55 gsm, determined according to the Basis Weight Test as disclosed herein.

26. The disposable diaper of claim 19, wherein the ratio of the basis weight of the first nonwoven web to the basis weight of the second nonwoven web is from 30/70 to 70/30.

27. The disposable diaper of claim 19, wherein the first nonwoven web and the second nonwoven web each have an opacity greater than 10%.

28. The disposable diaper of claim 19, wherein the first nonwoven web or the second nonwoven web has a static coefficient of friction equal to or less than 0.4.

29. The disposable diaper of claim 19, wherein the first nonwoven web or the second nonwoven web has a kinetic coefficient of friction equal to or less than 0.35.

30. The disposable diaper of claim 19, wherein the first nonwoven web and the second nonwoven web have respective static coefficients of friction that are within 30 percent of each other.

31. The disposable diaper of claim 19, wherein the first nonwoven web and the second nonwoven web have respective kinetic coefficients of friction that are within 30 percent of each other.

32. The disposable diaper of claim 19, wherein the first nonwoven web or the second nonwoven web comprises crimped fibers.

33. The disposable diaper of claim 32, wherein the crimped fibers comprise multicomponent fibers, and wherein the multicomponent fibers have at least two polymer components having differing properties and disposed in either side-by-side configuration or eccentric core/sheath configuration.

34. The disposable diaper of claim 19, wherein the first nonwoven web and the second nonwoven web have a combined basis weight of no more than 75 gsm, determined according to the Basis Weight Test as disclosed herein.

35. The disposable diaper of claim 19, wherein the first nonwoven web and the second nonwoven web have a combined basis weight of no more than 65 gsm, determined according to the Basis Weight Test as disclosed herein.

36. The disposable diaper of claim 19, wherein the first nonwoven web and the second nonwoven web have a combined basis weight of no more than 60 gsm, determined according to the Basis Weight Test as disclosed herein.

37. The disposable diaper of claim 19, wherein the absorbent core comprises:
   a first substrate;
   a second substrate; and
   a thermoplastic adhesive material disposed on or within the absorbent particulate polymer material;
   wherein the absorbent particulate polymer material is disposed intermediate the first and second substrates.

38. The disposable diaper of claim 19, wherein the ratio of the basis weight of the first nonwoven web to the basis weight of the second nonwoven web is from 40/60 to 60/40.

39. The disposable diaper of claim 19, wherein the ratio of the basis weight of the first nonwoven web to the basis weight of the second nonwoven web is from 45/55 to 55/45.

40. A package comprising a plurality of the disposable diapers of claim 19, wherein the package has an in-bag stack height of less than 85 mm, but greater than 75 mm, determined according to the In-Bag Stack Height Test as disclosed herein.

41. The disposable diaper of claim 19, wherein the first nonwoven web and the second nonwoven web each have an opacity greater than 40%.

42. The disposable diaper of claim 19, comprising an acquisition/distribution system positioned at least partially intermediate the topsheet and the absorbent core, wherein the acquisition distribution system is substantially cellulose free.

43. A disposable diaper, comprising:
   an innermost layer comprising a first nonwoven web, wherein the first nonwoven web has a compression loft of at least 30%, determined according to the Compression Loft Test as disclosed herein;
   an outermost layer comprising a second nonwoven web and a film, wherein the film has a WVTR value of less than 6,000 g/m$^2$ day, determined according to the WVTR Test as disclosed herein, and wherein the second nonwoven web has a compression loft of at least 30%, determined according to the Compression Loft Test as disclosed herein;
   a substantially cellulose free absorbent core positioned between the innermost layer and the outermost layer, wherein the substantially cellulose free absorbent core comprises:
      a first substrate;
      a second substrate;
      a thermoplastic adhesive material; and
      an absorbent particulate polymer material, wherein the thermoplastic adhesive material and the absorbent particulate polymer material are positioned intermediate the first and second substrates;
   wherein the first nonwoven web and the second nonwoven web have a combined basis weight of at least 45 gsm, determined according to the Basis Weight Test as disclosed herein; and
   wherein the disposable diaper has a relative humidity of less than 74%, after insults of a synthetic urine solution are applied to the diaper, determined according to the Humidity Test as disclosed herein.

44. The disposable diaper of claim 43, wherein the disposable diaper has a relative humidity of less than 70%, determined according to the Humidity Test as disclosed herein, and wherein the first nonwoven web and the second nonwoven web has a combined basis weight of at least 45 gsm, determined according to the Basis Weight Test as disclosed herein.

45. The disposable diaper of claim 43, wherein the substantially cellulose free absorbent core comprises no more than an immaterial amount of cellulose fibers.

46. A package comprising a plurality of the disposable diapers of claim 43, wherein the package has an in-bag stack height of less than 80 mm, determined according to the In-Bag Stack Height Test as disclosed herein.

* * * * *